United States Patent
Skowerski et al.

(10) Patent No.: US 10,974,236 B2
(45) Date of Patent: Apr. 13, 2021

(54) USE OF RUTHENIUM COMPLEXES IN OLEFIN METATHESIS REACTION

(71) Applicant: APEIRON SYNTHESIS S.A., Wroclaw (PL)

(72) Inventors: Krzysztof Skowerski, Jablonowo Pomorskie (PL); Rafal Gawin, Warsaw (PL); Michal Pawel Chwalba, Polajewo (PL)

(73) Assignee: APEIRON SYNTHESIS S.A., Wroclaw (PL)

( * ) Notice: Subject to any disclaimer, the term of this patent is extended or adjusted under 35 U.S.C. 154(b) by 0 days.

(21) Appl. No.: 16/348,721

(22) PCT Filed: Nov. 9, 2017

(86) PCT No.: PCT/IB2017/056992
§ 371 (c)(1),
(2) Date: May 9, 2019

(87) PCT Pub. No.: WO2018/087678
PCT Pub. Date: May 17, 2018

(65) Prior Publication Data
US 2019/0291089 A1    Sep. 26, 2019

(30) Foreign Application Priority Data
Nov. 10, 2016  (PL) .......................... 419421

(51) Int. Cl.
*B01J 31/22* (2006.01)
*C07C 67/347* (2006.01)
*C07C 67/475* (2006.01)
*C07C 253/30* (2006.01)
*C07F 15/00* (2006.01)
*C07C 67/333* (2006.01)
*B01J 31/18* (2006.01)
*C07C 6/04* (2006.01)

(52) U.S. Cl.
CPC ......... *B01J 31/2278* (2013.01); *B01J 31/181* (2013.01); *B01J 31/2204* (2013.01); *B01J 31/2273* (2013.01); *C07C 6/04* (2013.01); *C07C 67/333* (2013.01); *C07C 67/347* (2013.01); *C07C 67/475* (2013.01); *C07C 253/30* (2013.01); *C07F 15/0046* (2013.01); *B01J 2231/543* (2013.01); *B01J 2531/821* (2013.01); *B01J 2540/40* (2013.01); *B01J 2540/62* (2013.01); *C07C 2531/22* (2013.01); *C07C 2601/10* (2017.05); *Y02P 20/52* (2015.11)

(58) Field of Classification Search
CPC .................................................. B01J 31/2278
See application file for complete search history.

(56) References Cited

U.S. PATENT DOCUMENTS

2014/0088277 A1    3/2014   Stewart et al.
2014/0309433 A1    10/2014  Marx et al.

FOREIGN PATENT DOCUMENTS

WO    2017/055945    4/2017

OTHER PUBLICATIONS

Anderson et al., "Kinetic Selectivity of Olefin Metathesis Catalysts Bearing Cyclic (Alkyl) (Amino) Carbenes", Organometallics, 27(4): 563-566 (2008).
Gawin et al., "Bis(Cyclic Alkyl Amino Carbene) Ruthenium Complexes: A Versatile, Highly Efficient Tool for Olefin Metathesis", Angew. Chem. Int. Ed., 56(4): 981-986 (2017).
Gawin et al., "Cyclic Alkyl Amino Ruthenium Complexes—Efficient Catalysts for Macrocyclization and Acrylonitrile Cross Metathesis", ACS Catalysis, 7(8): 5443-5449 (2017).
International Search Report and Written Opinion of the International Searching Authority, dated Feb. 19, 2018 in corresponding International Patent Application No. PCT/IB2017/056992.
International Preliminary Report on Patentability, dated Feb. 2, 2019 in corresponding International Patent Application No. PCT/IB2017/056992.

*Primary Examiner* — Shawquia Jackson
(74) *Attorney, Agent, or Firm* — Wenderoth, Lind & Ponack, L.L.P.

(57) ABSTRACT

The invention relates to the use of ruthenium complexes, which are homogeneous catalysts and/or precatalysts of the olefin metathesis reaction, which lead to the production of alkenes containing an internal (non-terminal) double C=C bond.

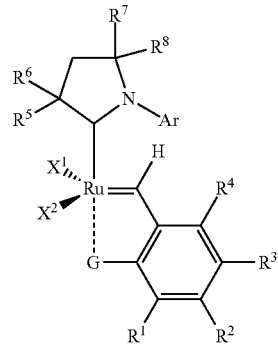

19 Claims, 1 Drawing Sheet

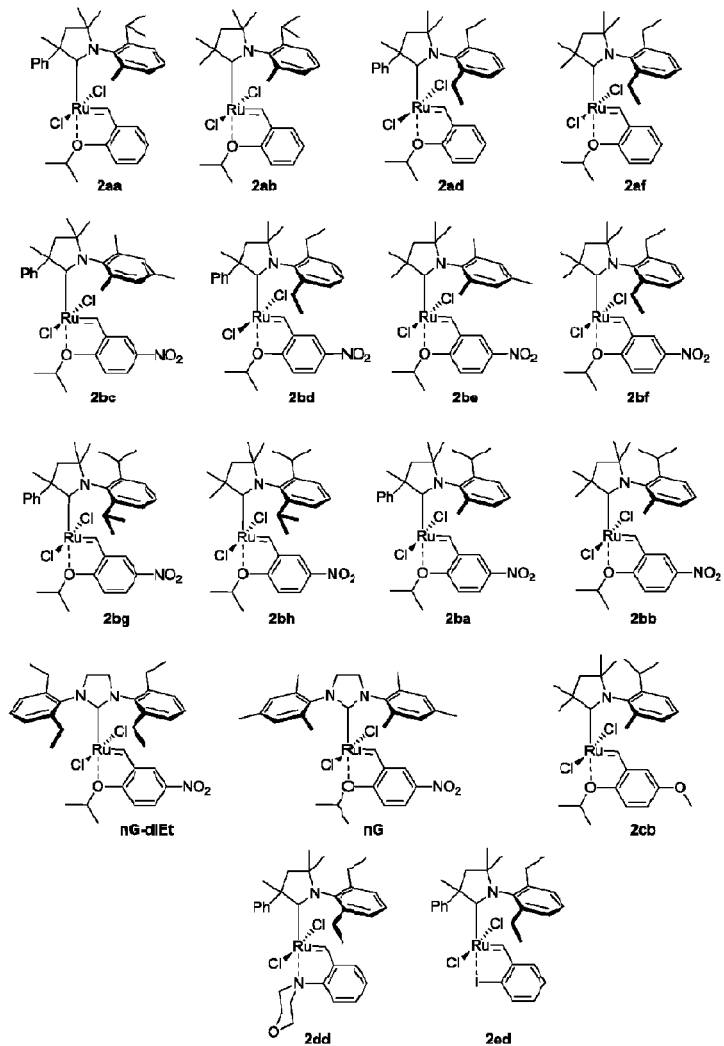
Ruthenium complexes indicated according to the system 2(ligand)(CAAC)

USE OF RUTHENIUM COMPLEXES IN OLEFIN METATHESIS REACTION

The invention relates to the use of ruthenium complexes acting as catalysts and/or precatalysts in the olefin metathesis reaction.

A number of ruthenium complexes are known in the art that allow to obtain internal olefins [R. H. Grubbs (Ed.), AG Wenzel (Ed.), D. J. O'Leary (Ed.), E. Khosravi (Ed.), Handbook of Olefin Metathesis, 2nd edition, 3 Volumes, 2015, John Wiley & Sons, Inc. 1608 pages], among which one should note the 1st, 2nd and 3rd generations, and complexes comprising two, identical or different, N-heterocyclic carbene ligands (NHCs). In ruthenium complexes, the active, 14-electron catalyst form comprises a neutral ligand that is a phosphine or NHC [Grubbs et al. *Chem. Rev.* 2010, 110, 1746-1787; Nolan et al. *Chem. Commun.* 2014, 50, 10355-10375].

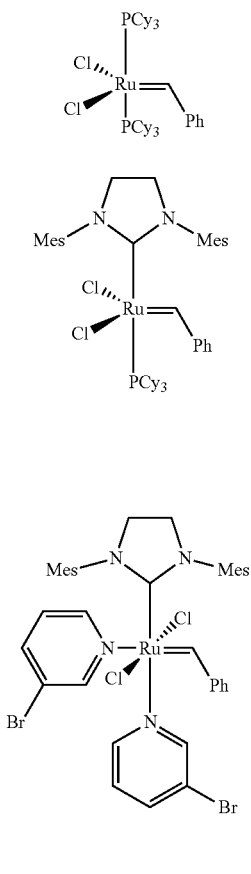

Gru-I

Gru-II

Gru-III

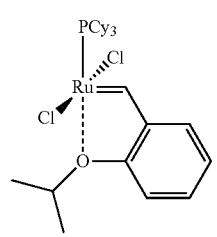

Hov-I

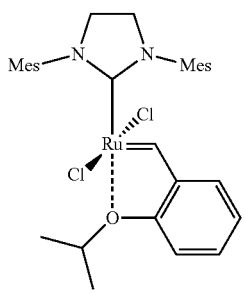

Hov-II

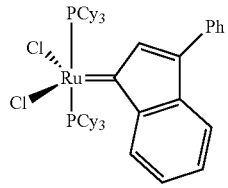

M1

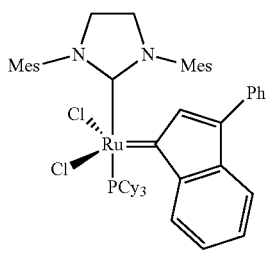

M2
(Ind-II)

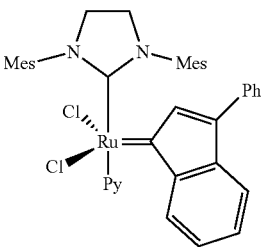

M31
(Ind-III)

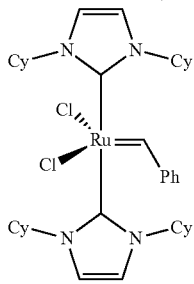

bis-NHC
(Herrmann)

2,4,6-trimetylofenyl
Mes = 2,4,6,-trimetylofenyl
Cy = cyclohexyl
Py = pyridine

The most versatile and effective complexes are those of the 2nd generation—the so-called Grubbs catalysts (Gru-II), Hoveydy-Grubbs (Hov-II) and Indenylidene (Indium II), i.e. those that contain one NHC type ligand in their structure.

Cross-metathesis (CM) reaction with acrylonitrile (and its derivatives) is one of the most demanding olefin metathesis processes, since acrylonitrile is considered to be the type 3 olefin in metathesis reactions [no homodimerisation—*J. Am. Chem. Soc.,* 2003, 125, 11360-11370]. On the other hand, CM of acrylonitrile with unsaturated esters, amides or other nitriles leads to the formation of bifunctional molecules with a considerable added value. For example, products of the CM of acrylonitrile with medium chain length esters containing a C=C terminal bond or with unsaturated fatty acid esters may be used to obtain aminoesters—monomers for the production of polyamids [Bruneau, P. H. Dixneuf et al., *ChemSusChem,* 2012, 5, 1410-1414, DOI:10.1002/cssc.201200086]. The most effective catalysts in an industrially significant cross-metathesis reaction with acrylonitrile [S. J. Connon and S. Blechert, *Chem. Int. Ed.* 2003, 42, 1900-1923, DOI:10.1002/anie.200200556], are Hov-II catalysts; even these complexes, however, allow for obtaining the maximum turn over number w (TON) of as little as 13,000 [*Monatsh. Chem.,* 2015, 146, 1107-1113, DOI: 10.1007/s00706-015-1480-1] which prevents this methodology from being industrially used. Steric or electron modifications of Hov-II complexes did not produce a powerful improvement in CM with acrylonitrile. The inability to significantly improve the efficiency of complexes of ruthenium with NHC (expressed as TON) in reactions leading to the formation of internal C=C bonds is a substantial problem in the art.

According to the state of the art, ruthenium complexes containing a cyclic alkyl amino carbene ligand (CAAC) are used for obtaining terminal olefins in the way of cross-metathesis reaction with ethylene. At the stage of early work, Grubbs and Bertrand used standard ring closing metathesis (RCM) to evaluate the activity of the obtained CAAC ruthenium complexes [*Angew. Chem., Int. Ed.,* 2007, 46, 7262-7265], using high volumes (1-5 mol %) of the catalyst. In the latest reports, the same authors determine the reactivity of the new ruthenium complexes containing the CAAC ligand by measuring the rate of their reaction with vinyl ether and do not attempt to synthesize the internal C=C bonds [US20140309433A1, *Angew. Chem. Int. Ed.,* 2015, 54, 1919-1923]. Other authors attempted to modify the CAAC ligand framework by introducing a sterically crowded isopropyl substituent into the main ring [Zhang, Shi et al, *Chem. Commun.,* 2013, 49, 9491-9493, DOI: 10.1039/C3CC45823G]. Authors of this report used a high ruthenium complex load in the RCM reaction.

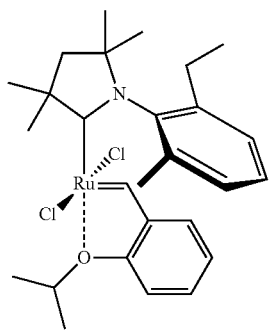

Hov-CAAC-1

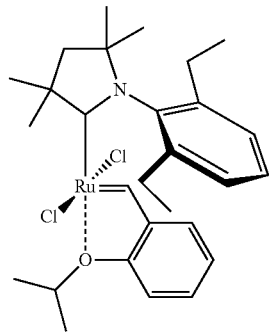

Hov-CAAC-2

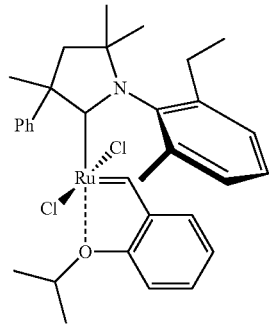

Hov-CAAC-3

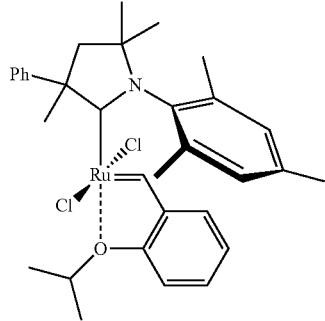

Hov-CAAC-4

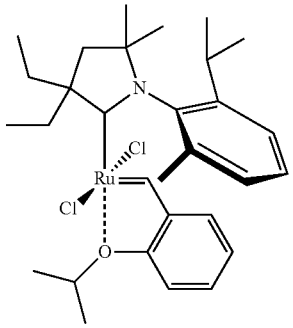

Hov-CAAC-5

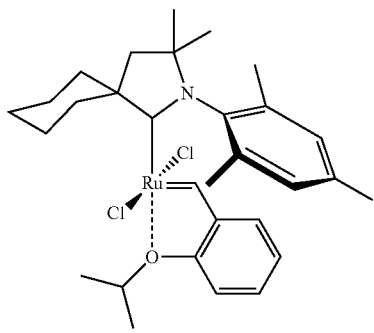

Hov-CAAC-6

It is also known that CAAC ligand-containing ruthenium complexes show a significantly greater degree of non-productive metathesis compared to most NHC-containing complexes [*J. Am. Chem. Soc.* 2010, 132, 8534-8535, DOI: 10.1021/ja1029045]. This is an undesirable characteristic in the synthesis of internal C=C bonds. Considering the current state of the art, it is therefore non-obvious to use the CAAC ruthenium complexes to obtain (in an economically advantageous manner) compounds containing an internal C=C bond.

In 2003, S. Blechert and others observed an advantageous effect of adding copper salt (I) on CM reactions catalyzed by Gru-II complexes with acrylonitrile [*Eur. J. Org. Chem.* 2003, 2225-2228, DOI:10.1002/ejoc.200300215]. The authors attributed the advantageous effect of the addition of copper salt (I) on the result of the CM reaction to the effect of scavenging phosphine from the reaction mixture and binding it into an insoluble complex.

In 2011, P. Dixneuf and Ch. Bruneau [*Green Chem.*, 2011, 13, 2258-2271, DOI:10.1039/C1GC153770] have attempted to utilise products of ethenolysis of vegetable oils in acrylonitrile reactions producing raw materials that contained nitrogen. Other attempts to utilise vegetable oil metathesis products have been described by the same authors in their next paper [*Green Chem.*, 2011, 13, 2911-2919, DOI: 10.1039/C1GC15569E], in which they subjected vegetable oil derivatives to various CM reactions with acrylonitrile and acrolein.

Yet another approach to obtaining compounds having two nitrile moieties in the molecule has been presented by Ch. Bruneau et al. [*Monatsh. Chem.*, 2015, 146, 1107-1113, DOI:10.1007/s00706-015-1480-1] CM reactions were carried out with acrylonitrile and 10-undecenonitrile in the presence of commercially available ruthenium complexes. Hitherto, for demanding CM reactions with acrylonitrile, no ruthenium complexes have been identified that would allow using that process on an industrial scale, with high yields and favorable selectivities.

Authors of papers and authors of the inventions cited above emphasise the positive effect of reduced substrate concentration (high dilution of C<0.1 M was used) on the reaction yield.

To sum up the state of the art, a substantial problem is posed by low efficiency (expressed as the TON value) in reactions that lead to the formation of internal C=C bonds. A particular case of a demanding reaction with high industrial potential is the CM with acrylonitrile, for which there are currently no alternative tools (in the form of more efficient homogeneous ruthenium catalysts) that would allow for improving the yield while maintaining a high selectivity of the process.

It has been observed that in the presence of selected CAAC-ruthenium complexes the CM reactions with acrylonitrile are characterised by a very high TON even at a concentration of 1 M, which can result in a significant reduction in process costs.

Surprisingly, it has been observed that CAAC ruthenium complexes promote the formation of internal C=C bonds with the catalyst loading of 0.1 mol %, and in some cases at <0.002 mol %.

Furthermore, it has been surprisingly found that the CAAC ligand structure has a key effect on the efficiency and selectivity of CM reactions with vinyl derivatives containing electron deficient partners (EDP), such as methyl acrylate or acrylonitrile.

It has been shown that ruthenium complexes containing CAAC ligands with the general formula 1, 1a show higher efficiency in forming internal C=C internal bonds than the complexes containing NHC ligand of formula 1b. In addition, the complexes containing ligand 1 have been shown to be much more effective and selective in CM reactions with acrylonitrile than analogs containing CAAC ligands with the general formula 1a and than NHC-containing complexes of formula 1b.

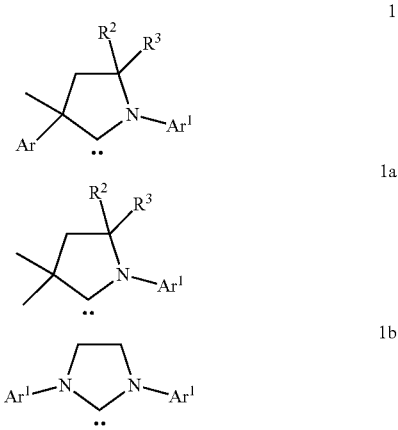

It has also been observed that substituents in the Ar$^1$ group greatly affect the efficiency and selectivity in CM reactions with EDP. Grubbs and Bertrand describe the superior efficiency of the 2aa and 2ab complexes in the ethenolysis reaction of methyl oleate leading to the formation of two terminal olefins.

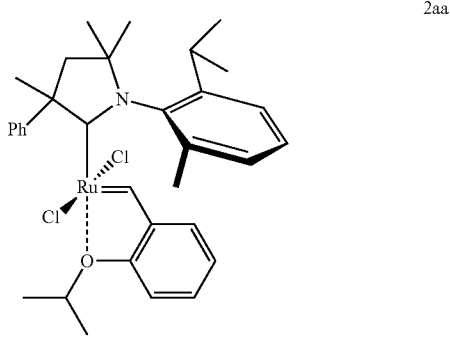

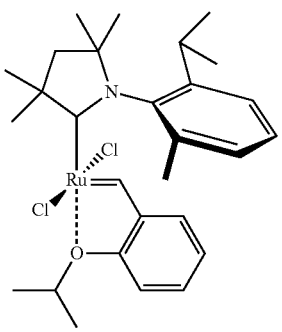

2ab

Surprisingly, in the CM reactions with EDP, the 2aa complex was significantly less efficient and selective than the complexes containing the Ar¹ moiety substituted in ortho positions with small or medium alkyl groups (Me, Et), such as the 2bc and 2bd complexes. Nevertheless, the phenyl substituent at the quaternary carbon atom made the 2aa complex more efficient and selective than the 2ab complex.

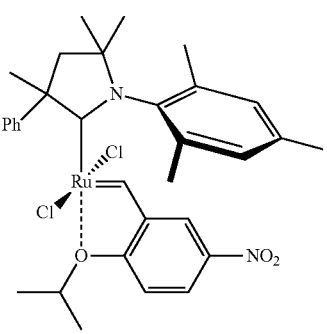

2bc

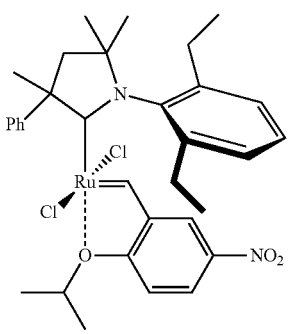

2bd

NHC ruthenium complexes containing at the nitrogen atoms of the NHC ligand a phenyl ring substituted in the ortho position with isopropyl groups (the so-called SIPr ligand) show very good activity and efficiency in the formation of internal C=C bonds. Similarly, benzylidene ruthenium CAAC complexes in which the nitrogen atom is substituted with 2,6-diisopropylphenyl show good and very good efficiency in the ethenolysis reaction. Surprisingly, a very low activity and efficiency of the CAAC complexes containing isopropyl groups in the ortho position of the Ar¹ have been observed in the reactions of the formation of internal C=C bonds. This activity is slightly increased at increased temperatures. For benzylidene CAAC complexes, a change in the activity is observed upon introduction of respective functional groups into the benzylidene ligand ring, known from benzylidene NHC complexes, is observed [for example: *Angew. Chem. Int. Ed.*, 2002, 41 (21), 4038-4040].

Another advantage of the ruthenium complexes of the invention is the superior selectivity in the reaction of acrylonitrile and an internal olefin. In a reaction of an asymmetrical internal olefin (e.g. of methyl oleate (MO) with acrylonitrile, the formation of two CM products with acrylonitrile, two CM products with ethylene and two MO homometathesis products is observed. The MO homomethasis products are the least desirable by-product, as they have less industrial applications than the terminal olefins, and their re-introduction to the process is unfavourable due to the reduced reactivity of internal olefins having a substantial ratio of the trans isomer. The complexes of the invention in the reaction of MO with acrylonitrile lead to the formation of homometathesis products in a quantity that is several fold lower.

DISCLOSURE OF THE ESSENCE OF THE INVENTION

The application, therefore, relates to the use of a compound of formula 2,

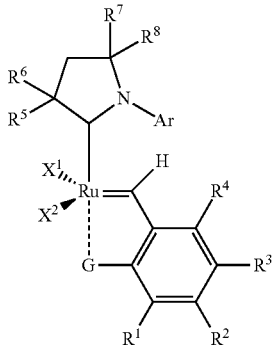

2 wherein:
$X^1$ and $X^2$ are each an anionic ligand;
G is a halogen atom or a substituent selected from OR', SR', S(O)R', S(O)$_2$R' N(R')(R''), P(R')(R'')(R'''), where R', R'' and R''' are the same or different $C_1$-$C_{25}$ alkyl group, $C_3$-$C_{12}$ cycloalkyl group, $C_1$-$C_{25}$ alkoxy group, $C_2$-$C_{25}$ alkenyl group, $C_1$-$C_{12}$ perfluoroalkyl, $C_5$-$C_{20}$ aryl, $C_5$-$C_{24}$ aryloxy, $C_2$-$C_{20}$ heterocyclyl, $C_4$-$C_{20}$, heteroaryl, $C_5$-$C_{20}$, or which may involve the formation of a substituted or non-substituted cyclic $C_4$-$C_{10}$ or policyclic $C_4$-$C_{12}$ systems, which are optionally substituted with at least one $C_1$-$C_{12}$ alkyl, $C_1$-$C_{12}$ perfluoroalkyl, $C_1$-$C_{12}$ alkoxy, $C_5$-$C_{24}$ aryloxy, $C_2$-$C_{20}$ heterocyclyl, $C_4$-$C_{20}$ heteroaryl, $C_5$-$C_{20}$ heteroaryloxy, may also be substituted with an ester (—COOR'), amide (—CONR'$_2$), formyl (—CHO), ketone (—COR'), hydroxamic (—CON(OR')(R')) groups, wherein R' is $C_1$-$C_{12}$ alkyl, $C_3$-$C_{12}$ cycloalkyl, $C_2$-$C_{12}$ alkenyl, $C_5$-$C_{20}$ aryl, which are optionally substituted with at least one $C_1$-$C_{12}$ alkyl, $C_1$-$C_{12}$ perfluoroalkyl, $C_1$-$C_{12}$ alkoxy, $C_5$-$C_{20}$ aryl, $C_5$-$C_{24}$ aryloxy, $C_7$-$C_{24}$ aralkyl, $C_2$-$C_{20}$ heterocycle, $C_4$-$C_{20}$, heteroaryl, $C_5$-$C_{20}$ heteroaryloxy, or a halogen atom;
Ar is an aryl group that is substituted by hydrogen atoms, or optionally is substituted by at least one $C_1$-$C_{12}$ alkyl, $C_1$-$C_{12}$ perfluoroalkyl, $C_1$-$C_{12}$ alkoxy, $C_5$-$C_{24}$ aryloxy, $C_2$-$C_{20}$ heterocyclic, $C_4$-$C_{20}$ heteroaryl, $C_5$-$C_{20}$ heteroaryloxy, $C_7$-$C_{24}$ aralkyl, $C_5$-$C_{24}$ perfluoroaryl groups, or a halogen atom;

$R^1$, $R^2$, $R^3$, $R^4$ are each a hydrogen atom, a (—S(O)R') sulphoxide group, a (—SO$_2$NR'$_2$) sulphonamide group, a (—P(O)(OR')$_2$) phosphonium group, a (—P(O)R'(OR')) phosphonium group, a (—P(OR')$_2$) phosphonous group, a (—PR'$_2$) phosphine group, a (—NO$_2$) nitro group, a (—NO) nitroso group, a (—COOH) carboxy group, a (—COOR') ester group, a (—CHO) formyl group, a (—COR') ketone group, a —NC(O)R' group, an amino group, an ammonium group, a (—OMe) alkoxy group, in which groups R' is $C_1$-$C_5$ alkyl, $C_1$-$C_5$ perfluoroalkyl, $C_5$-$C_{24}$ aryl, $C_7$-$C_{24}$ aralkyl, $C_5$-$C_{24}$ perfluoroaryl, $C_4$-$C_{20}$ heteroaryl, $C_5$-$C_{20}$ heteroaryloxy, and wherein $R^1$, $R^2$, $R^3$ and $R^4$ may be interconnected to form a cyclic system;

$R^5$, $R^6$, $R^7$ and $R^8$ are each a hydrogen atom or a $C_1$-$C_{25}$, alkyl, $C_3$-$C_{12}$ cycloalkyl, $C_1$-$C_5$ perfluoroalkyl, $C_2$-$C_{12}$ alkenyl, $C_5$-$C_{20}$, aryl $C_5$-$C_{24}$ aryloxy, $C_2$-$C_{20}$ heterocycle, $C_4$-$C_{20}$ heteroaryl, $C_5$-$C_{20}$ heteroaryloxy, $C_7$-$C_{24}$ aralkyl $C_5$-$C_{24}$, which are optionally substituted by at least one $C_1$-$C_{12}$ alkyl, $C_1$-$C_{12}$, perfluoroalkyl, $C_1$-$C_{12}$ alkoxy, $C_5$-$C_{24}$ aryloxy, $C_4$-$C_{20}$ heteroaryl, $C_5$-$C_{20}$ heteroaryloxy or a halogen atom; and wherein $R^5$ and $R^6$ and/or $R^7$ and $R^8$ may be interconnected to form a cyclic system;

in olefin metathesis reactions where at least one compound is formed as the main product containing at least one non-terminal double C=C bond, involving the process of contacting at least one type of olefin in the presence of a compound of formula 2.

Preferably, said compound is represented by formula 2

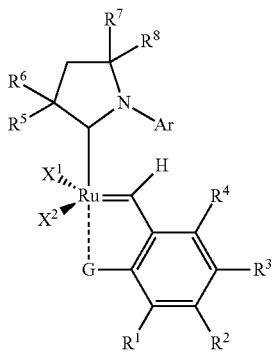

2 wherein:

$X^1$ and $X^2$ are halogen atoms,

G is a halogen atom or a substituent selected from the OR', N(R')(R") group, wherein R' and R" are the same or different $C_1$-$C_{12}$ alkyl, $C_3$-$C_{12}$ cycloalkyl, $C_2$-$C_{12}$ alkenyl, $C_5$-$C_{20}$ aryl, which are optionally substituted by at least one $C_1$-$C_{12}$ alkyl, $C_1$-$C_{12}$ perfluoroalkyl, $C_1$-$C_{12}$ alkoxy, $C_5$-$C_{24}$ aryloxy, $C_5$-$C_{20}$ heteroaryloxy;

$R^1$, $R^2$, $R^3$, $R^4$ are each a hydrogen atom, a (—S(O)R') sulphoxide group, a (—SO$_2$NR'$_2$) sulphonamide group, a (—P(O)(OR')$_2$) phosphonium group, a (—P(O)R'(OR')) phosphinium group, a (—P(OR')$_2$) phosphonous group, a (—PR'$_2$) phosphine group, a (—NO$_2$) nitro group, a (—NO) nitroso group, a (—COOH) carboxy group, a (—COOR') ester group, a (—CHO) formyl group, a (—COR') ketone group, a —NC(O)R' group, an amino group, an ammonium group, a (—OMe) alkoxy group, in which groups R' is $C_1$-$C_5$ alkyl, $C_1$-$C_5$ perfluoroalkyl, $C_5$-$C_{24}$ aryl, $C_7$-$C_{24}$ aralkyl, $C_5$-$C_{24}$ perfluoroaryl;

$R^5$, $R^6$, $R^7$ and $R^8$ are each a hydrogen atom or an $C_1$-$C_{25}$ alkyl, a $C_3$-$C_{12}$ cycloalkyl, a $C_2$-$C_{12}$ alkenyl, a $C_5$-$C_{20}$ aryl, a $C_1$-$C_5$ perfluoroalkyl, a $C_7$-$C_{24}$ aralkyl, a $C_5$-$C_{24}$ perfluoroaryl groups, which are optionally substituted by at least one $C_1$-$C_{12}$ alkyl, $C_1$-$C_{12}$ perfluoroalkyl, $C_1$-$C_{12}$ alkoxy, $C_5$-$C_{24}$ aryloxy, $C_5$-$C_{20}$ heteroaryloxy, or a halogen atom; and wherein $R^5$ and $R^6$ and/or $R^7$ and $R^8$ may be interconnected to form a cyclic system Preferably, said compound is represented by formula 2

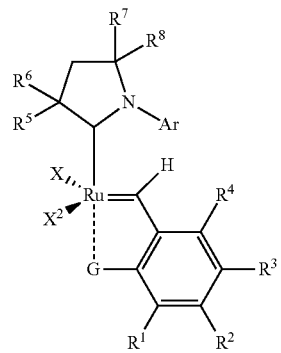

2 wherein:

$X^1$ and $X^2$ are halogen atoms,

G is a halogen atom or a substituent selected from the OR', N(R')(R") group, wherein R' is $C_1$-$C_{12}$ alkyl, $C_3$-$C_{12}$ cycloalkyl, $C_5$-$C_{20}$ aryl, which are optionally substituted by at least one $C_1$-$C_{12}$ alkyl, $C_1$-$C_{12}$ perfluoroalkyl, $C_1$-$C_{12}$ alkoxy, $C_5$-$C_{24}$ aryloxy, $C_5$-$C_{20}$ heteroaryloxy;

$R^1$, $R^2$, $R^3$, $R^4$ are each a hydrogen atom, a (—S(O)R') sulphoxide group, a (—SO$_2$NR'$_2$) sulphonamide group, a (—NO$_2$) nitro group, a (—COOR') ester group, a (—COR') ketone group, a —NC(O)R' group, an amino group, an ammonium group, a (—OMe) alkoxy group, in which groups R' is $C_1$-$C_5$ alkyl, $C_1$-$C_5$ perfluoroalkyl, $C_5$-$C_{24}$ aryl, $C_7$-$C_{24}$ aralkyl, $C_5$-$C_{24}$ perfluoroaryl;

$R^5$, $R^6$, $R^7$ and $R^8$ are each a hydrogen atom or an $C_1$-$C_{25}$ alkyl, a $C_3$-$C_{12}$ cycloalkyl, a $C_5$-$C_{20}$ aryl, a $C_7$-$C_{24}$ aralkyl, which are optionally substituted by at least one $C_1$-$C_{12}$ alkyl, $C_1$-$C_{12}$ perfluoroalkyl, $C_1$-$C_{12}$ alkoxy, $C_5$-$C_{24}$ aryloxy, $C_5$-$C_{20}$ heteroaryloxy, or a halogen atom; and wherein $R^5$ and $R^6$ and/or $R^7$ and $R^8$ may be interconnected to form a cyclic system Preferably, said compound is represented by formula 2

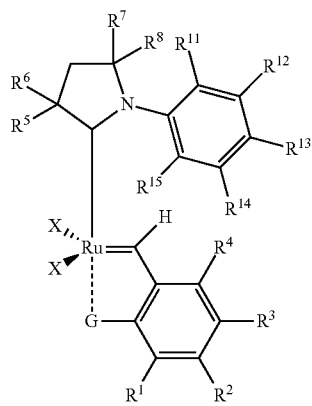

2 wherein:

X is an atom of chlorine or iodine

G is a halogen atom or a substituent selected from a OR', N(R')(R") group, wherein R' is $C_1$-$C_{12}$ alkyl, $C_3$-$C_{12}$ cycloalkyl, $C_5$-$C_{20}$ aryl, which are optionally substituted by at least one $C_1$-$C_{12}$ alkyl, $C_1$-$C_{12}$perfluoroalkyl, $C_1$-$C_{12}$ alkoxy, $C_5$-$C_{24}$, aryloxy, $C_5$-$C_{20}$ heteroaryloxy;

$R^1$, $R^2$, $R^3$, $R^4$ are each a hydrogen atom, a (—S(O)R') sulphoxide group, a (—SO$_2$NR'$_2$) sulphonamide group, a (—NO$_2$) nitro group, a (—COOR') ester group, a (—COR') ketone group, a —NC(O)R' group, an amino group, an ammonium group, a (—OR) alkoxy group, in which groups R' is $C_1$-$C_5$ alkyl, $C_1$-$C_5$ perfluoroalkyl, $C_5$-$C_{24}$ aryl, $C_7$-$C_{24}$ aralkyl, $C_5$-$C_{24}$ perfluoroaryl;

$R^5$, $R^6$, $R^7$ and $R^8$ are each a hydrogen atom or a $C_1$-$C_{25}$ alkyl, $C_3$-$C_{12}$ cycloalkyl, $C_5$-$C_{20}$ aryl, $C_7$-$C_{24}$ aralkyl, which are optionally substituted by at least one $C_1$-$C_{12}$ alkyl $C_1$-$C_{12}$ perfluoroalkyl, $C_1$-$C_{12}$ alkoxy, $C_5$-$C_{24}$ aryloxy, $C_5$-$C_{20}$, heteroaryloxy, or a halogen atom; and wherein $R^5$ and $R^6$ and/or $R^7$ and $R^8$ may be interconnected to form a cyclic system;

$R^{11}$, $R^{12}$, $R^{13}$, $R^{14}$ and $R^{15}$ are each a hydrogen atom, a halogen atom, a $C_1$-$C_{25}$ alkyl group, a $C_3$-$C_7$, cycloalkyl group, a $C_1$-$C_{25}$ alkoxy group, a $C_5$-$C_{24}$ perfluoroaryl group, $C_5$-$C_{20}$ heteroaryl group or a $C_2$-$C_{25}$ alkenyl group, and wherein the substituents $R^2$, $R^{2'}$, $R^3$, $R^{3'}$ and $R^4$ may be interconnected to form a substituted or non-substituted cyclic $C_4$-$C_{10}$ or policyclic $C_4$-$C_{12}$ system.

Preferably, said compound is represented by formula 2

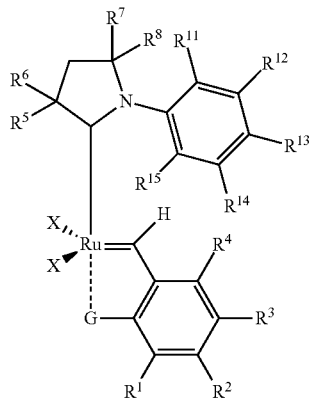

2 wherein:

X is an atom of chlorine or iodine

G is a halogen atom or a substituent selected from OR', N(R')(R"), wherein R' is $C_1$-$C_{12}$ alkyl, $C_3$-$C_{12}$ cycloalkyl, $C_5$-$C_{20}$ aryl, which are optionally substituted by at least one $C_1$-$C_{12}$ alkyl, $C_1$-$C_{12}$ perfluoroalkyl, $C_1$-$C_{12}$ alkoxy, $C_5$-$C_{24}$ aryloxy, $C_5$-$C_{20}$ heteroaryloxy;

$R^1$, $R^2$, $R^3$, $R^4$ are each a hydrogen atom, a (—S(O)R') sulphoxide group, a (—SO$_2$NR'$_2$) sulphonamide group, a (—NO$_2$) nitro group, a (—COOR') ester group, a (—COR') ketone group, a —NC(O)R' group, an amino group, an ammonium group, a (—OMe) alkoxy group, in which groups R' is $C_1$-$C_5$ alkyl, $C_1$-$C_5$ perfluoroalkyl, $C_5$-$C_{24}$ aryl, $C_7$-$C_{24}$ aralkyl, $C_5$-$C_{24}$ perfluoroaryl;

$R^5$, $R^6$, $R^7$ and $R^8$ are each a hydrogen atom or a $C_1$-$C_{25}$ alkyl, $C_3$-$C_{12}$ cycloalkyl, $C_5$-$C_{20}$ aryl, $C_7$-$C_{24}$ aralkyl groups, which are optionally substituted by at least one $C_1$-$C_{12}$ alkyl, $C_1$-$C_{12}$ perfluoroalkyl, $C_1$-$C_{12}$ alkoxy, $C_5$-$C_{24}$ aryloxy, $C_5$-$C_{20}$ heteroaryloxy, or a halogen atom; and wherein $R^5$ and $R^6$ and/or $R^7$ and $R^8$ may be interconnected to form a cyclic system $R^{11}$ and $R^{15}$ are each methyl, ethyl or isopropyl $R^{12}$, $R^{13}$, $R^{14}$ are each a hydrogen atom, a $C_1$-$C_{25}$ alkyl group, Preferably, said compound is represented by formula 2

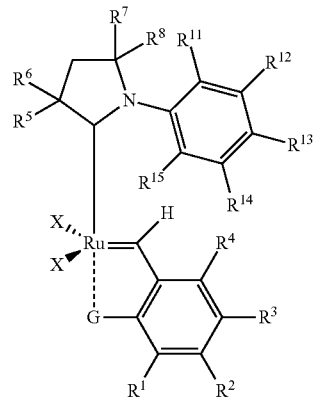

2 wherein:

X is an atom of chlorine or iodine

G is a halogen atom or a substituent selected from OR', N(R')(R"), wherein R' is $C_1$-$C_{12}$ alkyl, $C_3$-$C_{12}$ cycloalkyl, $C_5$-$C_{20}$ aryl, which are optionally substituted by at least one $C_1$-$C_{12}$ alkyl, $C_1$-$C_{12}$ perfluoroalkyl, $C_1$-$C_{12}$ alkoxy, $C_5$-$C_{24}$ aryloxy, $C_5$-$C_{20}$ heteroaryloxy;

$R^1$, $R^2$, $R^3$, $R^4$ are each a hydrogen atom, a (—S(O)R') sulphoxide group, a (—SO$_2$NR'$_2$) sulphonamide group, a (—NO$_2$) nitro group, a (—COOR') ester group, a (—COR') ketone group, a —NC(O)R' group, an ammonium group, a (—OMe) alkoxy group, in which groups R' is $C_1$-$C_5$ alkyl, $C_1$-$C_5$ perfluoroalkyl, $C_5$-$C_{24}$ aryl, $C_7$-$C_{24}$ aralkyl, $C_5$-$C_{24}$ perfluoroaryl;

$R^5$, $R^6$, $R^7$ and $R^8$ are each a hydrogen atom or a $C_1$-$C_{25}$ alkyl, $C_5$-$C_{20}$ aryl groups, which are optionally substituted by at least one $C_1$-$C_{12}$ alkyl, $C_1$-$C_{12}$ perfluoroalkyl, $C_1$-$C_{12}$ alkoxy, $C_5$-$C_{24}$ aryloxy, $C_5$-$C_{20}$ heteroaryloxy, or a halogen atom; and wherein $R^5$ and $R^6$ and/or $R^7$ and $R^8$ may be interconnected to form a cyclic system $R^{11}$ and $R^{15}$ are each methyl or ethyl;

$R^{12}$, $R^{13}$, $R^{14}$ are each a hydrogen atom, a $C_1$-$C_{25}$ alkyl group.

Preferably, the intercontacted olefins contain at least one nitrile moiety.

Preferably, one of the intercontacted olefins is acrylonitrile.

Preferably, an olefin containing at least one nitrile moiety is used in the cross-metathesis (CM) reaction.

Preferably, acrylonitrile is used in an amount of from 1 to 6 equivalents of the second olefin.

Preferably, acrylonitrile is used in an amount of from 1.05 to 2 equivalents of the second olefin.

Preferably, the reaction is conducted in an organic solvent such as toluene, benzene, mesitylene, dichloromethane, ethyl acetate, methyl acetate, tertbutyl methyl ether, cyclopentylmethyl ether, or with no solvent.

Preferably, the reaction is conducted at a temperature of from 20 to 150° C.

Preferably, the reaction is conducted at a temperature of from 40 to 120° C.

Preferably, the reaction is conducted at a temperature of from 40 to 90° C.

Preferably, the reaction is conducted over from 5 minutes to 24 hours.

Preferably, compound 2 is used in an amount of less than 0.1 mol %.

Preferably, compound 2 is added to the reaction mixture in portions and/or continuously using a pump.

Preferably, compound 2 is added to the reaction mixture as a solid and/or as a solution in an organic solvent.

Preferably, acrylonitrile is added to the reaction mixture in portions and/or continuously using a pump.

Preferably, the gaseous by-product of the reaction (ethylene, propylene, butylene) is actively removed from the reaction mixture using an inert gas or vacuum.

The invention will be presented in greater detail in preferred embodiments, with reference to the accompanying drawings, in which:

FIG. 1 shows the summary of olefin metathesis precatalysts and/or catalysts used according to the present invention.

TERMS

The terms used in the present description have the meanings as follows. Non-defined terms in this document have the meaning given and understood by a person skilled in the art in the light of the best knowledge held, of the present disclosure, and of the context of the description of the patent application. Unless it is indicated otherwise, the following conventional chemistry terms are used the present description that have the meanings as defined below.

The term "halogen atom" or "halogen" refers to an element selected from F, Cl, Br, I.

The term "carbene" refers to a particle containing a neutral carbon atom with a valence number of two and having two unpaired (triplet state) or paired (singlet state) valence electrons. The term "carbene" also includes carbene analogs in which the carbon atom is substituted by another chemical element such as boron, silicon, germanium, tin, lead, nitrogen, phosphorus, sulphur, selenium and tellurium.

The term "alkyl" refers to a saturated, linear or branched hydrocarbon substituent having the indicated number of carbon atoms. Examples of alkyl substituents include -methyl, -ethyl, -n-propyl, -n-butyl, -n-pentyl, -n-hexyl, -n-heptyl, -n-octyl, n-nonyl, and -n-decyl. Representative branched-($C_1$-$C_{10}$)alkyls include -isopropyl, -sec-butyl, -isobutyl, -tert-butyl, -isopentyl, -neopentyl, -1-methylobutyl, -2-methylobutyl, -3-methylobutyl, -1,1-dimethylopropyl, -1,2-dimethylopropyl, -1-methylopentyl, -2-methylopentyl, -3-methylopentyl, -4-methylopentyl, -1-ethylobutyl, -2-ethylobutyl, -3-ethylobutyl, -1,1-dimethylobutyl, -1,2-dimethylobutyl, 1,3-dimethylobutyl, -2,2-dimethylobutyl, -2,3-dimethylobutyl, -3,3-dimethylobutyl, -1-methylohexyl, 2-methylohexyl, -3-methylohexyl, -4-methylohexyl, -5-methylohexyl, -1,2-dimethylopentyl, -1,3-dimethylopentyl, -1,2-dimethylohexyl, -1,3-dimethylohexyl, -3,3-dimethylohexyl, 1,2-dimethyloheptyl, -1,3-dimethyloheptyl, -3,3-dimethyloheptyl and the like.

The term "alkoxy" refers to an alkyl substituent as defined above bound by an oxygen atom.

The term "perfluoroalkyl" refers to an alkyl group as defined above in which all the hydrogen atoms have been substituted by the same or different halogen atoms.

The term "cycloalkyl" refers to a saturated mono- or polycyclic hydrocarbon substituent having the indicated number of carbon atoms. Examples of cycloalkyl substituents include -cyclopropyl, -cyclobutyl, -cyclopentyl, -cyclohexyl, -cycloheptyl, -cyclooctyl, -cyclononyl, -cyclodecyl and the like.

The term "alkenyl" refers to a saturated, linear or branched non-cyclic hydrocarbon substituent of the indicated number of carbon atoms and containing at least one double carbon-carbon bond. Examples of alkenyl substituents include -vinyl, -allyl, -1-butenyl, -2-butenyl, -isobutylenyl, -1-pentenyl, -2-pentenyl, -3-methylo-1-butenyl, -2-methylo-2-butenyl, -2,3-dimethylo-2-butenyl, -1-hexenyl, -2-hexenyl, -3-hexenyl, -1-heptenyl, -2-heptenyl, -3-heptenyl, -1-octenyl, -2-octenyl, -3-octenyl, -1-nonenyl, -2-nonenyl, -3-nonenyl, -1-decenyl, -2-decenyl, -3-decenyl and the like.

The term "cycloalkenyl" refers to a saturated mono- or polycyclic hydrocarbon substituent of the indicated number of carbon atoms and containing at least one double carbon-carbon bond. Examples of cycloalkenyl substituents include cyclopentenyl, cyclopentadienyl, cyclohexenyl, cyclohexadienyl, cycloheptenyl, cycloheptadienyl, cycloheptatrienyl, cyclooctenyl, cyclooctadienyl, cyclooctatrienyl, cyclooctatetraenyl, cyclononenyl, cyclopentadienyl, cyclodecenyl, cyclodecadienyl and the like.

The term "alkynyl" refers to a saturated, linear or branched non-cyclic hydrocarbon substituent of the indicated number of carbon atoms and containing at least one triple carbon-carbon bond. Examples of alkynyl substituents include acetylenyl, propynyl, -1-butynyl, -2-butynyl, -1-pentynyl, -2-pentynyl, -3-methyl-1-butynyl, 4-pentynyl, -1-hexynyl, 2-hexynyl, -5-hexynyl and the like.

The term "cycloalkynyl" refers to a saturated mono- or polycyclic hydrocarbon substituent of the indicated number of carbon atoms and containing at least one triple carbon-carbon bond. Examples of cycloalkynyl substituents include cyclohexnyl, -cycloheptynyl, -cyclooctynyl and the like.

The term "aryl" refers to an aromatic mono- or polycyclic hydrocarbon substituent having the indicated number of carbon atoms. Examples of aryl substituents include phenyl, -tolyl, -xylyl, -naphthyl, -2,4,6-trimethylphenyl, -2-fluorophenyl, -4-fluorophenyl, -2,4,6-trifluorophenyl, -2,6-difluorophenyl, -4-nitrophenyl and the like.

The term "aralkyl" refers to an alkyl substituent as defined above substituted with at least one aryl as defined above. Examples of aralkyl substituents include benzyl, -diphenylmethyl, -triphenylmethyl and the like.

The term "heteroaryl" refers to an aromatic mono- or polycyclic hydrocarbon substituent having the indicated number of carbon atoms, in which at least one carbon atom is substituted by a heteroatom selected from O, N and S atoms. Examples of heteroaryl substituents include furyl, thienyl, imidazolyl, oxazolyl, thiazolyl, isoxazolyl, triazolyl, oxadiazolyl, thiadiazolyl, tetrazolyl, pyridyl, pyrimidyl, triazinyl, indolyl, benzo[b]furyl, benzo[b]thienyl, indazolyl, benzoimidazolyl, azaindolyl, quinolyl, isoquinolyl, carbazolyl and the like.

The term "heterocycle" refers to a saturated or partially non-saturated, mono- or polycyclic hydrocarbon substituent having the indicated number of carbon atoms, in which at least one carbon atom is substituted by a heteroatom selected from O, N and S atoms. Examples of heterocyclic substituents include furyl, thiophenyl, pyrrolyl, oxazolyl, imidazolyl, thiazolyl, isoxazolyl, pyrazolyl, isothiazolyl, triazinyl, pyrrolidinonyl, pyrrolidinyl, hydantoinyl, oxiranyl, oxetanyl, tetrahydrofuranyl, tetrahydrothiophenyl, quinolinyl, isoquinolinyl, chromonyl, coumarinyl, indolyl, indolizinyl, benzo[b]furanyl, benzo[b]thiophenyl, indazolyl, purinyl, 4H-quinolizinyl, isoquinolyl, quinolyl, phthalazinyl, naphthyridinyl, carbazolyl, β-carbolinyl and the like.

The term "neutral ligand" refers to a non-charged substituent capable of coordinating with a metallic centre (the ruthenium atom). Examples of such ligands may include: amines, phosphines and oxides thereof, alkyl and aryl phosphites and phosphates, arsines and oxides thereof, ethers, alkyl and aryl sulphides, coordinated hydrocarbons, alkyl and aryl halides.

The term "anionic ligand" refers to a substituent capable of coordinating with a metallic centre (the ruthenium atom) with a charge capable of partially or completely compensating the charge of the metallic centre. Examples of such ligands may include fluoride, chloride, bromide, iodide, cyanide, cyanate and thiocyanate anions, carboxylic acid anions, alcohol anions, phenolic anions, thiol and thiophenol anions, delocalized charge hydrocarbon anions (e.g. cyclopentadiene), (organo)sulphuric and (organo)phosphoric acid anions and esters thereof (such as, for example, alkylsulphonic and aryl sulphonic acid anions, alkylphosphoric and arylphosphoric acid anions, sulphuric acid alkyl and aryl ester anions, phosphoric acid alkyl and aryl ester anions, alkylphosphoric and arylphosphoric alkyl and aryl ester anions). Optionally, the anionic ligand may have interconnected $L^1$, $L^2$ and $L^3$ groups, such as the catechol anion, the acetylacetone anion, the salicylaldehyde anion. Anionic ligands ($X^1$, $X^2$) and neutral ligands ($L^1$, $L^2$, $L^3$) may be interconnected to form multidentate ligands, such as a bidentate ligand ($X^1$—$X^2$), a tridentate ligand ($X^1$—$X^2$-$L^1$) a tetradentate ligand ($X^1$—$X^2$-$L^1$-$L^2$), a bidentate ligand ($X^1$-$L^1$), a tridentate ligand ($X^1$-$L^1$-$L^2$), a tetradentate ligand ($X^1$-$L^1$-$L^2$-$L^3$), a bidentate ligand ($L^1$-$L^2$), a tridentate ligand ($L^1$-$L^2$-$L^3$). Examples of such ligands include catechol anion, acetylacetone anion and salicylaldehyde anion.

The term "heteroatom" refers to an atom selected from the group comprising an atom of oxygen, sulphur, nitrogen, phosphorus and the like.

The term "chlorinated solvent" refers to a solvent, the structure of which comprises at least one atom of for example fluorine, chlorine, bromine and iodine; preferably more than one. Examples of such solvents include dichloromethane, chloroform, tetrachloromethane (carbon tetrachloride), 1,2-dichloroethane, chlorobenzene, perfluorobenzene, perfluorotoluene, freons and the like.

The term "organic non-polar solvent" refers to a solvent characterised by non-existent or very low dipole momentum. Examples of such solvents include pentane, hexane, octane, nonane, decane, benzene, toluene, xylene and the like.

The term "organic polar solvent" refers to a solvent characterised by a dipole momentum substantially greater than zero. Examples of such solvents include dimethylformamide (DMF), tetrahydrofuran (THF) and its derivatives, diethyl ether, dichloromethane, ethyl acetate, chloroform, alcohols (MeOH, EtOH or i-PrOH) and the like.

The term "GC" refers to gas chromatography.
The term "HPLC" refers to high performance liquid chromatography, and solvents designated as "HPLC" solvents refer to solvents having sufficient purity for HPLC analysis.
The term "NMR" refers to nuclear magnetic resonance.
The term "NHC" refers to N-heterocyclic carbene.
The term "CAAC" refers to cyclic alkyl amino carbene ligand.
The term "DEDAM" refers to diethyl diallylmalonate.

The term "precatalyst" refers to, in relation to ruthenium complexes, a 16-electron chemical compound which, after the step of dissociation of one ligand or reorganisation of the molecule, is converted to the 14-electron olefin metathesis catalyst as such, which is active in the catalytic cycle.

EMBODIMENTS OF THE INVENTION

The following examples are provided solely for the purpose of illustrating the invention and for clarifying the individual aspects thereof, and not with the intention to limit it, and should not be considered to be equivalent to the total scope thereof as defined in the appended claims. In the examples below, unless otherwise indicated, standard materials and methods were employed as used in the art or it was proceeded according to the manufacturer's recommendations for particular reagents and methods.

Ethyl undecanoate (EU), 1-decene, acrylonitrile, methyl acrylate, methyl oleate (MO) and methyl stearate are commercially available compounds. EU and MO were distilled under reduced pressure and stored over activated alumina. 1-decene, acrylonitrile and methyl acrylate were dried using 4 Å molecular sieves and deoxygenated under argon. All reactions were conducted under argon. Toluene was washed with citric acid, water, dried using 4 Å molecular sieves and deoxygenated under argon.

The composition of reaction mixtures was tested by gas chromatography using a PerkinElmer Clarus 680 GC equipped with the GL Sciences InertCap® 5MS/NP capillary column.

The individual components of reaction mixtures were identified by comparing retention times with commercial standards or standards isolated from reaction mixtures for which the structure was confirmed by NMR.

The FID detector response coefficients for the individual ingredients of mixtures were used for calculations (determination method in Example I). The area under the peak of each component in the chromatogram was converted to a percentage in the mixture using the calculated response coefficients.

Example I

CM Reaction of Methyl Acrylate with Ethyl Undecanoate (S1)

To the solution of S1 (0.637 g, 3 mmol, 1 eq.), methyl acrylate (1.08 ml, 12 mmol, 4 eq.) and methyl stearate (internal standard) in toluene (11 ml) at 70° C. under argon, a solution of precatalyst (0.365 mg, 0.02 mol %, 200 ppm) in toluene (50 µl) was added in four portions at 20-minute intervals. The mixture was stirred for 2 hours. A sample was taken to which 3 drops of ethyl vinyl ether were added to deactivate the catalyst. The sample was analysed by gas chromatography.

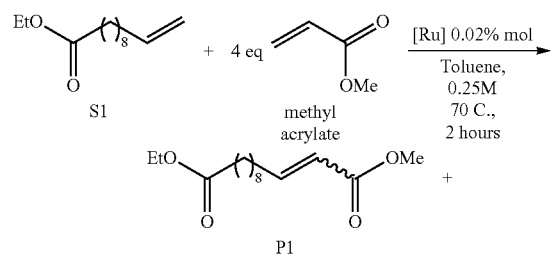

-continued

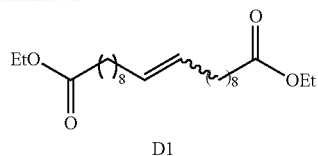

D1

TABLE 1a

Experimental results of the CM reaction of methyl acrylate with S1

| precatalyst [Ru] | Conversion [%] | P1 [%] | D1 [%] | Selectivity to P1 [%] |
|---|---|---|---|---|
| 2be | 43 | 6 | 36 | 14 |
| 2bc | 64 | 36 | 26 | 58 |
| 2bf | 43 | 4 | 37 | 9 |
| 2bd | 63 | 28 | 33 | 45 |
| 2bh | 0 | — | — | — |
| 2bg | 0 | — | — | — |
| 2bb | 63 | 12 | 50 | 19 |
| 2ba | 61 | 15 | 44 | 25 |

In order to determine the response coefficients of the FID detector for the individual ingredients of reaction mixtures, two aliquots containing a mixture of the S1 substrate, the desired product P1 and the by-product D1 were prepared. The resulting mixtures were diluted with toluene to a volume of 10 ml and analysed by gas chromatography. The area under the PP peak for each ingredient (the mean of five injections) was divided by the weight of the ingredient in the aliquot taking into account its purity, to give an absolute response coefficient for the Rf ingredient. Assuming a S1 substrate coefficient of $R_f=1$, relative Rf coefficients for the other ingredients were determined. The mean Rf for the two aliquots was determined for calculations.

TABLE 1b

Method for determining the response coefficients of the FID detector for the individual ingredients of a reaction mixture.

| Ingredient | Aliquot weight m [mg] | Purity per GC [%] | Area under the peak PP [µV × s] | Absolute response coefficient Rf = PP/ (m × purity) [µV × s/mg] | Response coefficient for S1 Rf |
|---|---|---|---|---|---|
| Aliquot A: | | | | | |
| S1 | 27.95 | 98.4 | 41101.6 | 1494.5 | 1.00 |
| P1 | 26.58 | 98.9 | 36961.0 | 1406.0 | 0.94 |
| D1 | 27.57 | 98.8 | 45458.4 | 1668.9 | 1.12 |
| Aliquot B: | | | | | |
| S1 | 27.39 | 98.4 | 127135.9 | 4717.2 | 1.00 |
| P1 | 28.86 | 98.9 | 123728.6 | 4334.9 | 0.92 |
| D1 | 28.19 | 98.8 | 142693.4 | 5123.3 | 1.09 |
| Mean Rf of the two aliquots: | | | | | |
| S1 | | | | | 1.00 |
| P1 | | | | | 0.93 |
| D1 | | | | | 1.10 |

In further calculations, the area under the peak of each ingredient in the chromatogram was converted to a percentage in the mixture using the calculated response coefficients.

The selectivity of the reaction (S) was determined from the following formula:

$$S = 100 \times \frac{n_{P1}}{(n_{P1} + 2 \times n_{dimer})}$$

where n is the number of moles

The conversion of reaction (C) was determined from the following formula:

$$C = 100 \times \left(1 - \frac{\left(\frac{PP_{S1}}{PP_{IS}}\right)}{\left(\frac{PP_{S1^0}}{PP_{IS^0}}\right)}\right)$$

where:

$PP_{S1}{}^0$ and $PP_{S1}$ is the area under the peak of the substrate at the beginning of the reaction and at its end.

$PP_{IS}{}^0$ and $PP_{IS}$ is the area under the peak of the internal standard (methyl stearate) at the beginning of the reaction and at its end.

Example II

CM Reaction of Methyl Acrylate with S1 in Increased Temperature

The reaction was carried out according to the procedure described in Example I at 100° C.

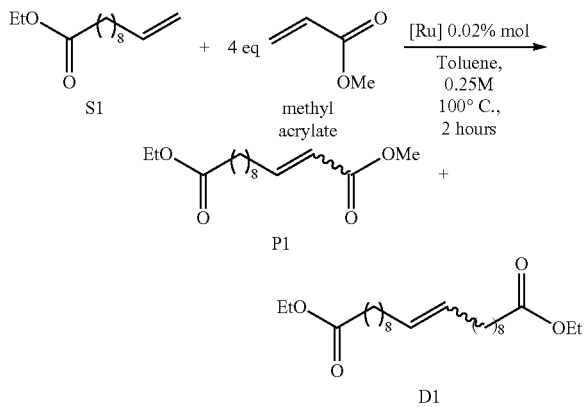

TABLE 2

Experimental results of the CM reaction of methyl acrylate with S1 in increased temp.

| precatalyst [Ru] | Conversion [%] | P1 [%] | D1 [%] | Selectivity to P1 [%] |
|---|---|---|---|---|
| 2bh | 7 | 0.3 | 5.4 | 4.5 |
| 2bg | 12 | 0.4 | 7.2 | 5.1 |

Example III

CM Reaction of Acrylonitrile with S1

To the solution of S1 (0.335 g, 1.58 mmol, 1 eq.), acrylonitrile (0.207 ml, 3.16 mmol, 2 molar eq.) and methyl stearate (internal standard) in toluene (15.5 ml) at 70° C. under argon, a solution of precatalyst (0.03 mol %, 300 ppm) in toluene (4×50 µl) was added in four portions at 5-minute intervals. The mixture was stirred for 2 hours. A sample was taken to which 3 drops of ethyl vinyl ether were added to deactivate the catalyst. The sample was analysed by gas chromatography.

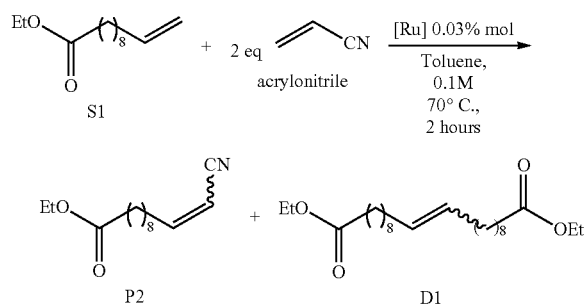

TABLE 3

Experimental results of the CM reaction of acrylonitrile with S1

| precatalyst [Ru] | Conversion [%] | P2 [%] | D1 [%] | Selectivity to P2 [%] |
|---|---|---|---|---|
| 2be | 46 | 33 | 13 | 71 |
| 2bc | 86 | 83 | 3 | 97 |
| 2bf | 49 | 29 | 20 | 59 |
| 2bd | 87 | 84 | 3 | 96 |
| 2bb | 43 | 22 | 21 | 51 |
| 2ba | 69 | 60 | 9 | 87 |

Example IV

CM Reaction of Acrylonitrile with S1 in Increased Temperature

The reaction was carried out according to the procedure described in Example III at 100° C.

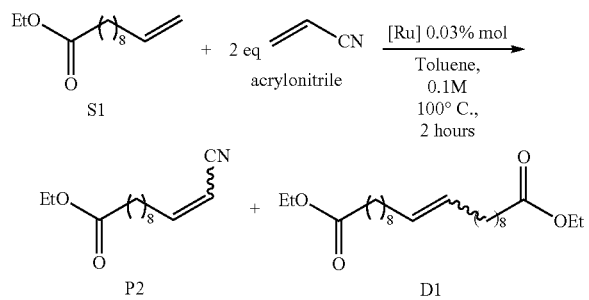

TABLE 4

Experimental results of the CM reaction of acrylonitrile with S1 in increased temp.

| Precatalyst [Ru] | Conversion [%] | P1 [%] | D1 [%] | Selectivity to P2 [%] |
|---|---|---|---|---|
| 2bh | 21 | 7 | 14 | 33 |
| 2bg | 25 | 13 | 12 | 51 |

Example V

CM Reaction of Acrylonitrile with S1—Effect of the S1 Concentration

To the solution of S1 (0.335 g, 1.58 mmol, 1 molar eq.), acrylonitrile (0.207 ml, 3.16 mmol, 2 molar eq.) and methyl stearate (internal standard) in the appropriate volume of toluene at 70° C. under argon, a solution of precatalyst (0.03 mol %, 300 ppm) in toluene (50 µl) was added in one portion. The mixture was stirred for 2 hours. The sample was analysed by gas chromatography.

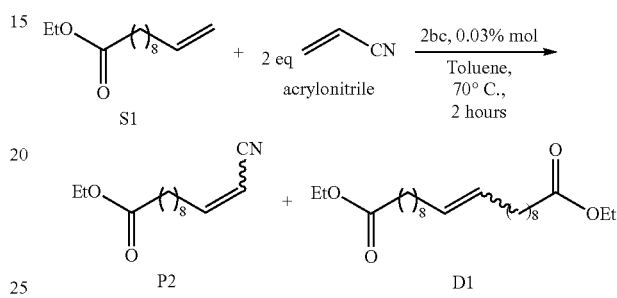

TABLE 5

Experimental results of the CM reaction of acrylonitrile with S1 in various concentrations.

| $C^0_{S1}$ [M] | Conversion [%] | P2 [%] | D1 [%] | Selectivity to P2 [%] |
|---|---|---|---|---|
| 0.1 | 86 | 83 | 3 | 97 |
| 0.25 | 95 | 92 | 3 | 97 |
| 1 | 87 | 82 | 5 | 94 |

Example VI

CM Reaction of Acrylonitrile with S1—Effect of the Acrylonitrile Volume

To the solution of S1 (0.335 g, 1.58 mmol, 1 molar eq.), acrylonitrile (1,1 or 2 or 4 molar eq.) and methyl stearate (internal standard) in ($C^0_{S1}$ 0.25 M) at 70° C. under argon, a solution of precatalyst (0.0075 mol %, 75 ppm) in toluene (50 µl) was added in one portion. The mixture was stirred for 2 hours. A sample was taken to which 3 drops of ethyl vinyl ether were added to deactivate the catalyst. The sample was analysed by gas chromatography.

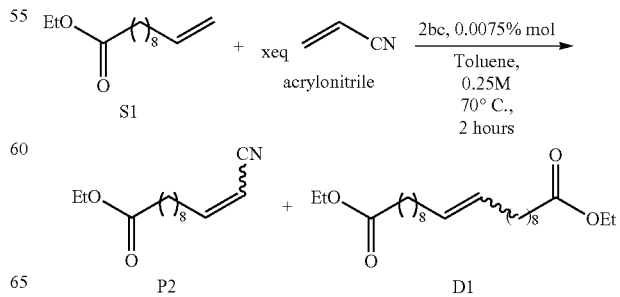

TABLE 6

Experimental results of the CM reaction of acrylonitrile with S1 - varying volume of acrylonitrile.

| acrylonitrile [eq.] | Conversion [%] | P2 [%] | D1 [%] | Selectivity to P2 [%] | TON |
|---|---|---|---|---|---|
| 1.1 | 87 | 81 | 6 | 93 | 10800 |
| 2 | 84 | 80 | 4 | 95 | 10667 |
| 4 | 75 | 72 | 3 | 97 | 9600 |

Example VII

CM Reaction of Acrylonitrile with S1—Effect of the S1 Concentration Comparison of the Complexes of the Invention with the Standard nG Complex.

To a solution of S1 (1.606 g, 7.56 mmol, 1 molar eq.), acrylonitrile (0.991 ml, 15.13 mmol, 2 molar eq.) and methyl stearate (internal standard) in toluene ($C^0_{S1}$ 0.1 or 0.25 M) at 70° C. under argon a solution of the precatalyst in toluene was added. For reactions catalysed with 0.015 mol % of the ruthenium complex, the precatalyst solution was added in four portions at 5-minute intervals. For reactions catalysed with 0.0075 mol % of the ruthenium complex, the precatalyst solution was added dropwise over 1 h using a syringe. For the reaction catalysed with 0.0025 mol % of the ruthenium complex, the precatalyst solution was added dropwise over 1 h using a syringe pump. The total reaction time was in each case 2 h. A sample was taken to which 3 drops of ethyl vinyl ether were added to deactivate the catalyst. The sample was analysed by gas chromatography.

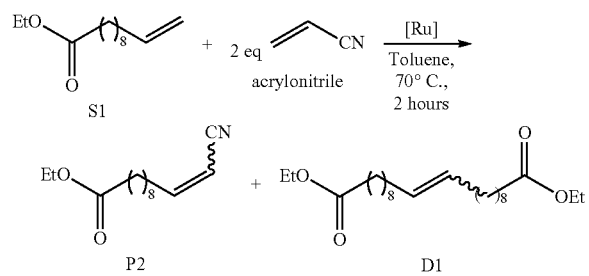

TABLE 7

Experimental results of the CM reaction of acrylonitrile with S1 - comparison of variables

| Precatalyst [Ru] (mol %) | $C_{S1}$ [M] | Conversion [%] | P2 [%] | D1 [%] | Select. to P2 [%] | TON |
|---|---|---|---|---|---|---|
| 2bc, 0.015 | 0.1 | 88 | 85 | 3 | 96.5 | 5667 |
| 2bc, 0.015 | 0.25 | 93 | 90 | 3 | 97.1 | 6000 |
| 2bc, 0.0075 | 0.1 | 82 | 78 | 4 | 95.4 | 10400 |
| 2bc, 0.0075 | 0.25 | 84 | 80 | 4 | 95.3 | 10667 |
| nG, 0.0075 | 0.25 | 27 | 26 | 1 | 96.1 | 3467 |
| 2ad, 0.0075 | 0.25 | 86 | 81 | 5 | 93.9 | 10800 |
| 2af, 0.0075 | 0.25 | 46 | 21 | 25 | 45.0 | 2800 |
| 2bc, 0.0025[a] | 0.25 | 48 | 43 | 5 | 89.9 | 17200 |

[a]The reaction mixture was gently blown with argon to actively remove released ethylene

Example VIII

CM Reaction of Acrylonitrile with S1—Effect of the Catalyst Type and Volume & Manner of Adding Acrylonitrile To a solution of S1 (1.606 g, 7.56 mmol, 1 molar eq.), acrylonitrile (0.495 ml, 1 molar eq.) and methyl stearate (internal standard) in toluene (23.8 ml) at 70° C. under argon, the precatalyst solution (0.0025 mol %, 25 ppm) in toluene (3 ml) and acrylonitrile solution (1 molar eq.) in toluene (3 ml solution volume) were added dropwise using a syringe pump over 1 hour. The reaction mixture was gently blown with argon to actively remove released ethylene. The total reaction time was in each case 2 h. A sample was taken to which 3 drops of ethyl vinyl ether were added to deactivate the catalyst. The sample was analysed by gas chromatography.

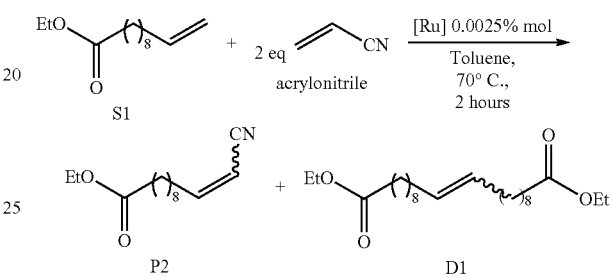

TABLE 8

Experimental results of the CM reaction of acrylonitrile with S1

| precatalyst [Ru] | Conversion [%] | P2 [%] | D1 [%] | Selectivity to P2 [%] | TON |
|---|---|---|---|---|---|
| 2bc | 63 | 56 | 7 | 89 | 22400 |
| 2bd | 73 | 62 | 11 | 84 | 24800 |

Example IX

CM Reaction of Acrylonitrile with S1—Effect of the Temperature

To a solution of S1 (1.606 g, 7.56 mmol, 1 molar eq.), acrylonitrile (0.495 ml, 7.56 mmol, 1 molar eq.) and methyl stearate (internal standard) in toluene ($C^0_{S1}$ 0.25 M) under argon, the precatalyst solution in toluene (1 ml) and acrylonitrile (1 molar eq.) were added dropwise over 1 h. The reaction mixture, in which 0.002 mol % of the precatalyst was used, was gently blown with argon to actively remove ethylene. The total reaction time was in each case 2 h. A sample was taken to which 3 drops of ethyl vinyl ether were added to deactivate the catalyst. The sample was analysed by gas chromatography.

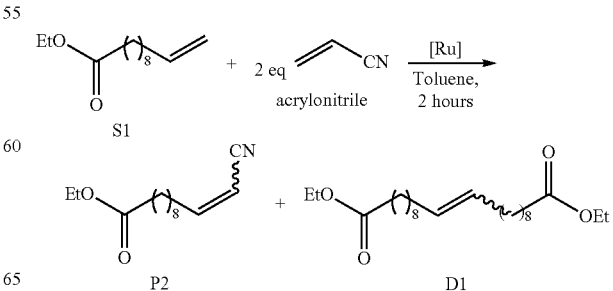

TABLE 9

Results of CM of acrylonitrile with S1 in various temperatures.

| precatalyst [Ru] (mol %) | Temp. [° C.] | Conversion [%] | P2 [%] | D1 [%] | Select. To P2 [%] | TON |
|---|---|---|---|---|---|---|
| 2bd, 0.005 | 70 | 69 | 60 | 9 | 87 | 12000 |
| 2bd, 0.005 | 85 | 79 | 69 | 10 | 88 | 13800 |
| 2bd, 0.005 | 100 | 3 | 2 | 1 | 60 | 400 |
| 2bd, 0.002 | 85 | 71 | 57 | 14 | 80 | 28500 |

Example X

CM Reaction of Methyl Acrylate with Ethyl Undecanoate (S1)

To a solution of S2 (1.506 g, 5.08 mmol, 1 molar eq.) and acrylonitrile (0.666 ml, 10.16 mmol, 2 molar eq.) in toluene (12 ml, $C^0_{S1}$ 0.4 M), the precatalyst solution (0.0125 mol, 125 ppm) in toluene (6 ml) and acrylonitrile solution (2.5 molar eq.) in toluene (6 ml) were added dropwise over 2.5 hours. The reaction mixture was gently blown with argon to actively remove released ethylene. After 3.5 hours from the beginning of the reaction, a sample was taken, to which 3 drops of ethyl vinyl ether were added to deactivate the catalyst. The sample was analysed by gas chromatography.

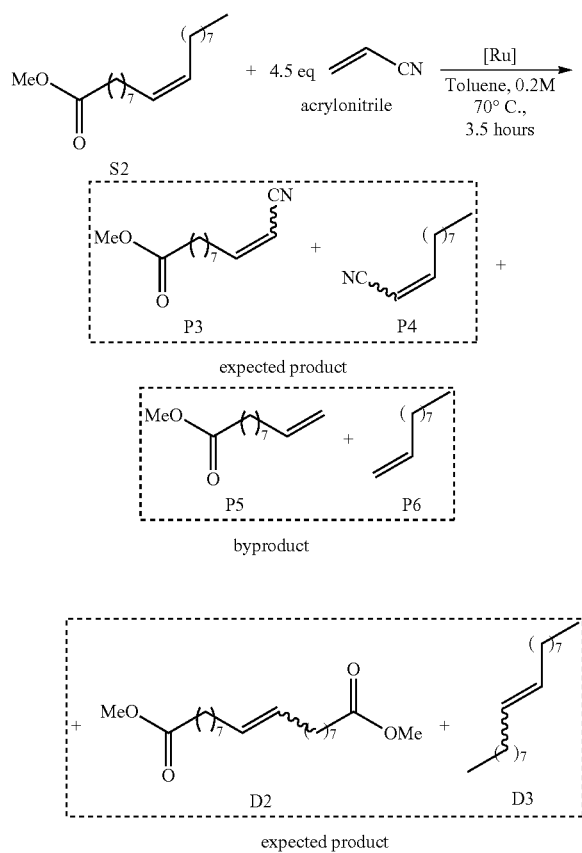

TABLE 10

Experimental results of the CM reaction of acrylonitrile with S2

| precatalyst [Ru], % mol | P3 [%] (E/Z) | P4 [%] (E/Z) | P5 + P6 [%] | D2 + D3 [%] | S2 [%] | selectivity to P3 + P4 [%] |
|---|---|---|---|---|---|---|
| 2bc, 0.01 | 35 (1/2) | 34 (1/2) | 16 | 2 | 13 | 79 |
| 2bc, 0.0125 | 37 (1/2) | 37 (1/2) | 14 | 2 | 9 | 82 |
| nG 0.01 | 19 (1/3) | 19 (1/3) | 19 | 9 | 35 | 58 |
| nG, 0.0125 | 21 (1/3) | 21 (1/3) | 20 | 9 | 30 | 59 |

Example XI

CM Reaction of 1-Decene (P6) with Acrylonitrile

To a solution of 1-decene (2.109 g, 15.04 mmol), acrylonitrile (0.985 ml, 15.04 mmol, 1 molar eq.) and methyl stearate (internal standard) in toluene (29 ml, $C^0_{1\text{-}decene}$ 0.5 M) at 70° C., a solution of the 2bd complex (0.0075 mol %, 75 ppm) in toluene (1 ml) using a syringe and (using a second syringe) acrylonitrile (1 molar eq.) were added over 1 hour. The mixture was stirred for one more hour at the same temperature. A sample was taken to which 3 drops of ethyl vinyl ether were added to deactivate the catalyst. The sample was analysed by gas chromatography.

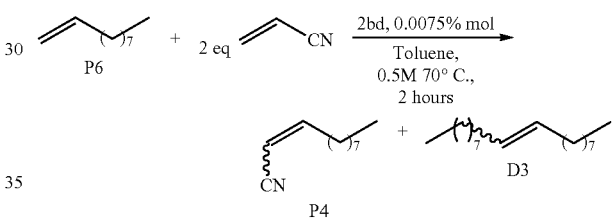

TABLE 11

Experimental results of the CM reaction of acrylonitrile with P6

| Conversion [%] | P4 [%] (E/Z) | D3 [%] | Selectivity to P4 [%] | TON |
|---|---|---|---|---|
| 91 | 84 (1/4) | 7 | 92 | 11200 |

Example XII

RCM Reaction of Diethyl Diallylmalonate (S3)

To a solution of S3 (0.240 g, 1.0 mmol) in toluene (10 ml) at 29° C., the precatalyst solution (0.1 mol %) in toluene (50 µl) was added in one portion. At required intervals, samples were taken of the reaction mixture to which a few drops of ethyl vinyl ether were added to deactivate the catalyst. The samples were analysed by gas chromatography.

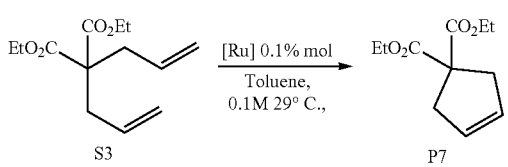

TABLE 12

Experimental results of the CM reaction of methyl acrylate with S1

| Time [min] | 2bc | 2be | 2bd | 2bf | 2af | 2bg | 2bh | 2ba | 2bb | 2ab | 2cb |
|---|---|---|---|---|---|---|---|---|---|---|---|
| 2.5 | 90 | 20 | 96 | — | — | — | — | 80 | — | — | — |
| 5 | 99 | 48 | 99 | 10 | 6 | 0.5 | 1 | 98 | 9 | 6 | 13 |
| 10 | 100 | 77 | 100 | 32 | 19 | 0.9 | 1 | 99 | 31 | 16 | 39 |
| 20 | — | 92 | — | 63 | 43 | 1.8 | 1 | 100 | 71 | 39 | 77 |
| 30 | — | 95 | — | 76 | 63 | 3 | — | — | 86 | 54 | 91 |
| 45 | — | 97 | — | 85 | 77 | 5 | 4 | — | 93 | 68 | 97 |
| 60 | — | 98 | — | 90 | 84 | 10 | 6 | — | 95 | 77 | 97 |

Example XIII

Homometathesis Reaction of the S1 Substrate to D1

A mixture of S1 (3.0 g, 14.13 mmol) with methyl stearate (internal standard) was placed under argon in a round bottom flask. After heating the mixture to 60° C., a solution of precatalyst in toluene was added at 15-minute intervals (2+2+1+1+1+1 ppm, total of 8 ppm). The mixture was stirred for 2 hours. Samples were taken to which a few drops of ethyl vinyl ether were added to deactivate the catalyst. The samples were analysed by gas chromatography.

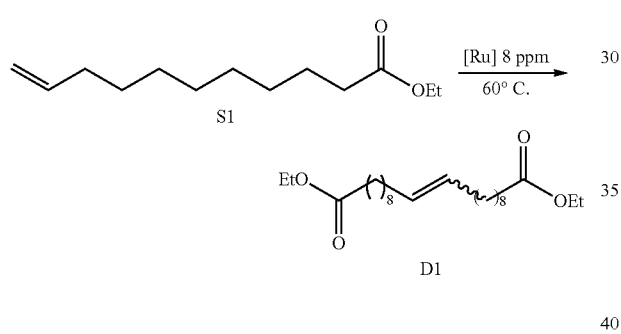

TABLE 13

Experimental results of the homodimerization reaction of S1

| precatalyst [Ru] | Conversion [%] | D1 [%] | Selectivity to D1 [%] | TON |
|---|---|---|---|---|
| 2bd | 75 | 67 | 89 | 41875 |
| 2bf | 82 | 77 | 94 | 48125 |
| nG-diEt | 48 | 42 | 88 | 26250 |

Example XIV

Reaction for Preparing Complex 2bc

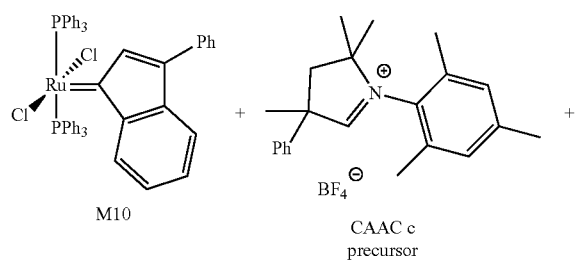

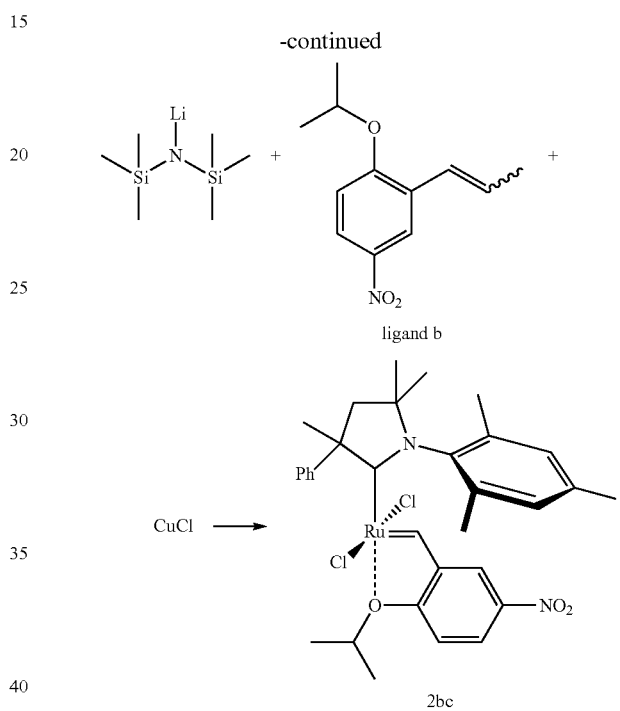

To CAAC c precursor (2.10 g, 5.34 mmol, 2 molar eq.) dry deoxygenated toluene (48 ml) was added under argon. The mixture was heated to 80° C. and a solution of LiHMDS in toluene (1 M, 5.34 ml, 5.34 mmol, 2 molar eq.) was added. After 1 minute, a solid M10 complex (2.37 g, 2.67 mmol, 1 molar eq.) was added. After 2 minutes the mixture was cooled to 60° C. Benzylidene ligand b was added (0.709 g, 3.20 mmol, 1.2 molar eq.) and CuCl (0.925 g, 9.35 mmol, 3.5 molar eq.). The mixture was stirred for 5 minutes at 60° C. and cooled to room temperature. The crude product was isolated by column chromatography on silica gel (eluent: toluene). The green fraction was collected and concentrated to dryness. The residue was dissolved in ethyl acetate and filtered. The solvent was evaporated, and the residue was washed with isopropanol and dried under highly reduced pressure to give a green crystalline solid—the 2bc precatalyst (0.455 g, 25%). Mixture of A:B isomers=2.2:1

Due to the very complex $^1$H NMR spectrum, only the chemical shifts of the characteristic benzylidene protons are indicated: A isomer: singlet 17.73 ppm; B isomer: singlet 16.16 ppm ($C_6D_6$).

HRMS: ESI was calculated for $C_{32}H_{38}N_2O_3NaCl_2Ru$ [M+Na]$^+$: 693.1201. found: 693.1179.

Elemental analysis: calculated for $C_{32}H_{38}N_2Cl_2O_3Ru$: C, 57.31; H, 5.71; N, 4.18; Cl, 10.57. found: C, 57.43; H, 5.72; N, 4.14; Cl, 10.4.

Example XV

Reaction for Preparing Complex 2be

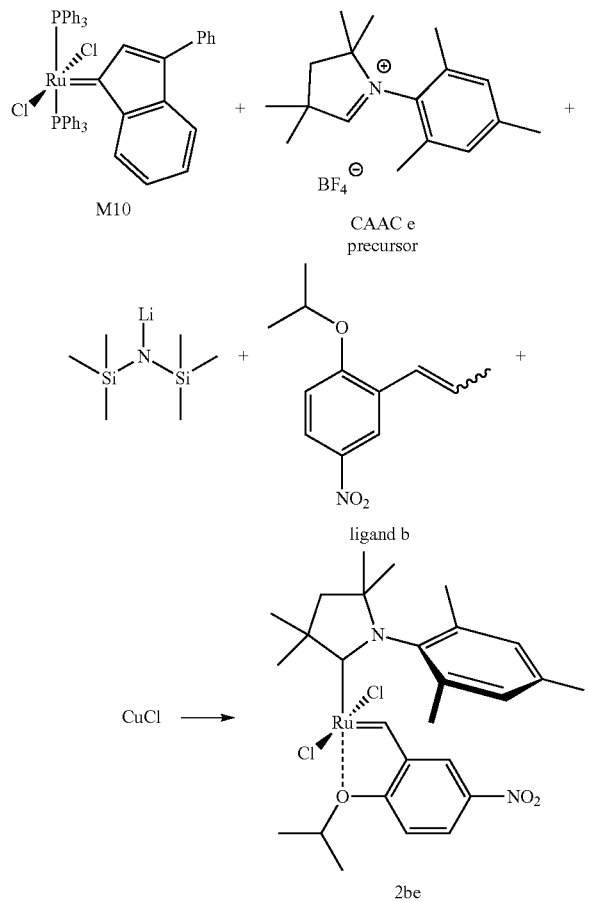

2be

To CAAC e precursor (1.66 g, 5.0 mmol, 2 molar eq.) dry deoxygenated toluene (20 ml) was added under argon. The mixture was heated to 80° C. and a solution of LiHMDS in toluene (1 M, 5.0 ml, 5.0 mmol, 2 molar eq.) was added. After 1 minute, a solid M10 complex (2.22 g, 2.5 mmol, 1 molar eq.) was added. After 2 minutes benzylidene ligand b (0.664 g, 3.0 mmol, 1.2 molar eq.) and CuCl (0.866 g, 8.75 mmol, 3.5 molar eq.) were added. The mixture was stirred for 30 minutes at 80° C. and cooled to room temperature. The crude product was isolated by column chromatography on silica gel (eluent: toluene). The green fraction was collected and concentrated to dryness. The residue was dissolved in ethyl acetate and filtered. The solvent was evaporated, and the residue was dissolved in methylene chloride and excess isopropanol was added. The methylene chloride was slowly removed under reduced pressure—the resulting crystals were filtered off and washed in a minimum volume of isopropanol. This was dried under highly reduced pressure to give a green crystalline solid—the 2be precatalyst (0.215 g, 14%).

$^1$H NMR (CD$_2$Cl$_2$, 500 MHz): δ=16.12 (s, 1H), 8.48 (dd, J=9.1; 2.7 Hz, 1H), 7.75 (d, J=2.8 Hz, 1H), 7.20 (s, 2H), 7.08 (d, J=9.1 Hz, 1H), 5.25 (septet, J=6.1 Hz, 1H), 2.54 (s, 3H), 2.21 (s, 2H), 2.19 (s, 6H), 2.05 (s, 6H), 1.74 (d, J=6.2 Hz, 6H), 1.43 (s, 6H).

$^{13}$C NMR (CD$_2$Cl$_2$, 125 MHz): δ=292.6, 264.1, 156.7, 144.2, 143.3, 139.7, 138.5, 137.9, 131.2, 125.7, 118.6, 113.7, 79.6, 78.1, 56.5, 52.4, 29.7, 29.3, 22.3, 21.2, 20.9.

HRMS-ESI was calculated for $C_{27}H_{36}N_2O_3NaCl_2Ru$ [M+Na]$^+$: 631.1044. found: 631.1028.

Elemental analysis: calculated for $C_{27}H_{36}N_2Cl_2O_3Ru$: C, 53.29; H, 5.96; N, 4.60; Cl, 11.65. found: C, 53.21; H, 5.93; N, 4.53; Cl, 11.61.

Example XVI

Reaction for Preparing Complex 2bd

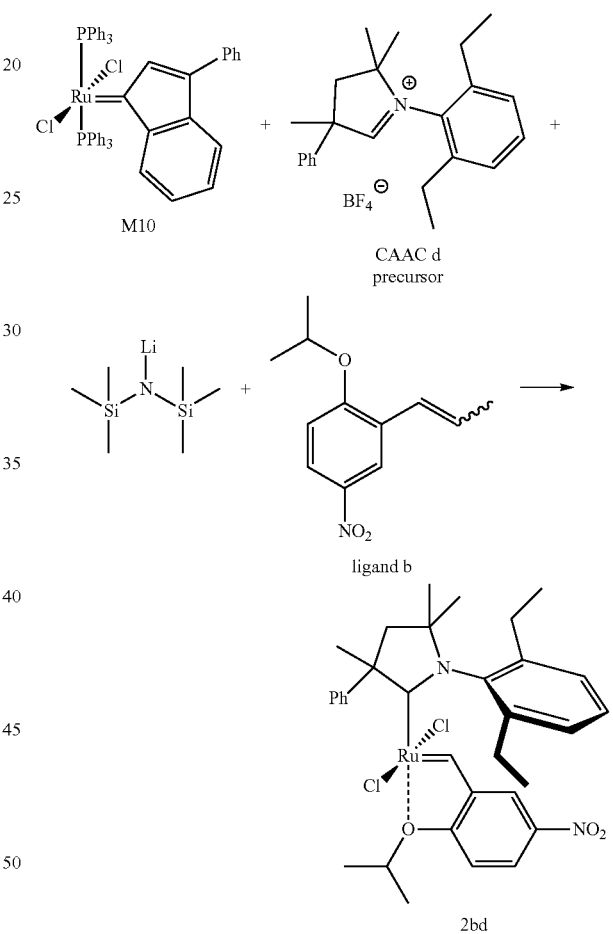

2bd

To CAAC d precursor (2.44 g, 6.0 mmol, 2 molar eq.) dry deoxygenated toluene (24 ml) was added under argon. The mixture was heated to 80° C. and a solution of LiHMDS in toluene (1 M, 6.0 ml, 6.0 mmol, 2 molar eq.) was added. After 1 minute, a solid M10 complex (2.66 g, 3.0 mmol, 1 molar eq.) was added. After 2 minutes, benzylidene ligand b (1.33 g, 6.0 mmol, 2.0 molar eq.) was added. The mixture was stirred for 30 minutes at 105° C. and cooled to room temperature. The crude product was isolated by column chromatography on silica gel (eluent: toluene). The green fraction was collected and concentrated to dryness. The residue was washed with a mixture of ethyl acetate-cyclohexane 5:95, and then dissolved in methylene chloride and excess isopropanol was added. The methylene chloride was slowly removed under reduced pressure—the resulting crystals were filtered off and washed in a minimum volume of isopropanol. This was dried under highly reduced pressure to give a green crystalline solid—the 2bd precatalyst (0.495 g, 24%).

$^1$H NMR (C$_6$D$_6$, 500 MHz): δ=[17.73 (s), 16.37 (s), 1H], 8.27 (br. s, 1H), 7.89 (dd, J=9.1; 2.7 Hz, 1H), 7.78 (br. s, 1H), 7.48 (br. s, 1H), 7.36-7.16 (m, 6H), 6.03 (d, J=9.1 Hz, 1H), 4.43-4.33 (m, 1H), 2.95-1.80 (m, 8H), 1.50-0.60 (m, 19H).

$^{13}$C NMR (C$_6$D$_6$, 125 MHz): δ=292.2, 262.4, 157.0, 144.0, 143.4, 139.1, 130.0, 129.7, 127.9, 127.6, 125.5, 118.2, 113.4, 78.4, 77.3, 63.7, 49.2, 31.1, 27.9, 27.6, 26.3, 25.9, 24.9, 22.5, 15.5, 14.9.

HRMS: ESI was calculated for C$_{33}$H$_{40}$N$_2$O$_3$ClRu [M−Cl]$^+$: 649.1771. found: 649.1746.

Elemental analysis: calculated for C$_{33}$H$_{40}$N$_2$Cl$_2$O$_3$Ru: C, 57.89; H, 5.89; N, 4.09; Cl, 10.36. found: C, 57.98; H, 5.99; N, 4.08; Cl, 10.44.

Example XVII

Reaction for Preparing Complex 2bf

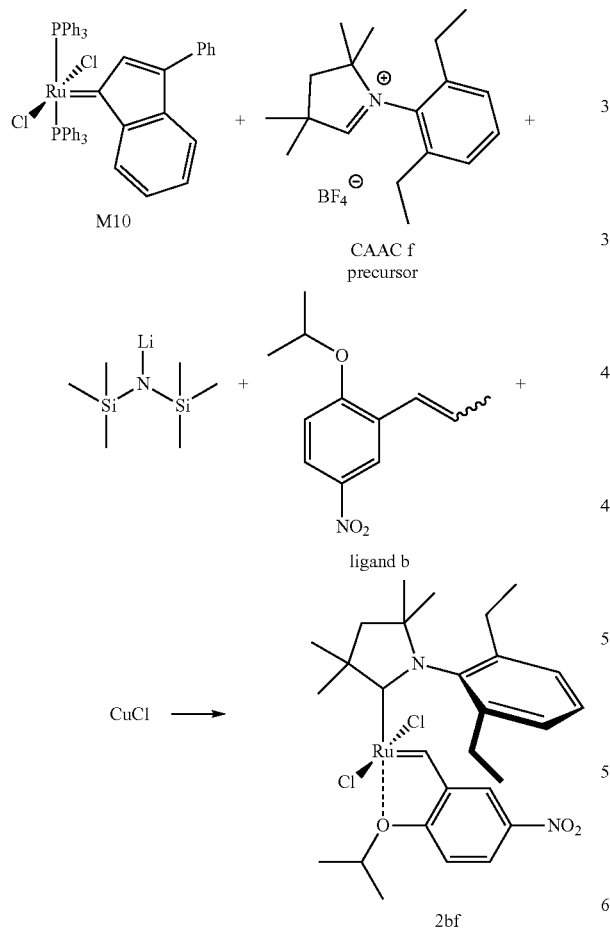

2bf

To CAAC f precursor (3.45 g, 10.0 mmol, 2 molar eq.) dry deoxygenated toluene (40 ml) was added under argon. The mixture was heated to 80° C. and a solution of LiHMDS in toluene (1 M, 10.0 ml, 10.0 mmol, 2 molar eq.) was added. After 1 minute, a solid M10 complex (4.43 g, 5.0 mmol, 1 molar eq.) was added. After 2 minutes the mixture was cooled to 60° C. Benzylidene ligand b (1.33 g, 6.0 mmol, 1.2 molar eq.) and CuCl (1.73 g, 17.5 mmol, 3.5 molar eq.) were added. The mixture was stirred for 5 minutes at 60° C. and cooled to room temperature. The crude product was isolated by column chromatography on silica gel (eluent: toluene). The green fraction was collected and concentrated to dryness. The residue was dissolved in ethyl acetate and filtered. The solvent was evaporated, and the residue was washed with isopropanol and dried under highly reduced pressure to give a green crystalline solid—the 2bf precatalyst (1.57 g, 50%).

$^1$H NMR (CD$_2$Cl$_2$, 500 MHz): δ=16.29 (s, 1H), 8.46 (dd, J=9.1; 2.7 Hz, 1H), 7.72 (d, J=2.8 Hz, 1H), 7.20 (s, 2H), 7.08 (d, J=8.7 Hz, 1H), 5.26 (septet, J=6.1 Hz, 1H), 2.61 (s, 3H), −2.49 (s, 2H), 2.21 (s, 6H), 2.07 (s, 6H), 1.77 (d, J=6.2 Hz, 6H), 1.33 (s, 6H).

$^{13}$C NMR (CD$_2$Cl$_2$, 125 MHz): δ=290.4, 263.8, 165.6, 157.1, 143.7, 143.4, 138.8, 129.9, 127.7, 125.7, 118.3, 113.7, 79.4, 78.2, 56.5, 52.3, 29.9, 28.9, 25.3, 22.4, 14.9.

HRMS: ESI was calculated for C$_{28}$H$_{39}$N$_2$O$_3$Ru [M−2Cl+H]$^+$: 553.2006. found: 553.2004.

Elemental analysis: calculated for C$_{28}$H$_{38}$N$_2$Cl$_2$O$_3$Ru: C, 54.02; H, 6.15; N, 4.50; Cl, 11.39. found: C, 54.18; H, 6.09; N, 4.42; Cl, 11.20.

Example XVIII

Reaction for Preparing Complex 2ad

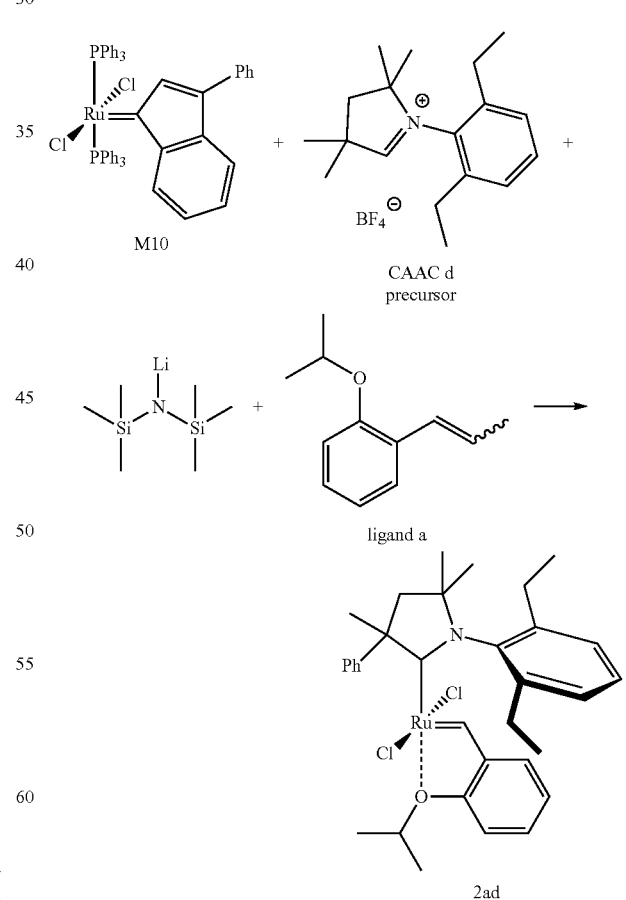

2ad

To CAAC d precursor (0,407 g, 1.0 mmol, 2 molar eq.) dry deoxygenated toluene (4 ml) was added under argon.

The mixture was heated to 80° C. and a solution of LiHMDS in toluene (1 M, 1.0 ml, 1.0 mmol, 2 molar eq.) was added. After 1 minute, a solid M10 complex (0.443 g, 0.5 mmol, 1 molar eq.) was added. After 2 minutes, benzylidene ligand b (0.176 g, 1.0 mmol, 2.0 molar eq.) was added. The mixture was stirred for 30 minutes at 105° C. and cooled to room temperature. The crude product was isolated by column chromatography on silica gel (eluent: toluene). The green fraction was collected and concentrated to dryness. The residue was dissolved in methylene chloride and excess isopropanol was added. The methylene chloride was slowly removed under reduced pressure—the resulting crystals were filtered off and washed in a minimum volume of isopropanol. This was dried under highly reduced pressure to give a green crystalline solid—the 2ad precatalyst (0.151 g, 47%). Mixture of A:B isomers=1:3

$^1$H NMR (C$_6$D$_6$, 500 MHz): δ=[17.89 (s, 0.25H, A isomer), 16.52 (s, 0.75H, B isomer), 1H], 8.55-7.70 (m, 2H), 7.60-7.18 (m, 6H), 7.12-7.07 (m, 1H), 6.98-6.84 (m, 1H), 6.68-6.43 (m, 1H), 6.38 (d, J=8.3 Hz, 1H), 4.60-4.45 (m, 1H), 3.10-2.00 (m, 8H), 2.00-1.14 (m, 9H), 1.07 (s, 5H), 0.99 (s, 3H), 0.85 (br. s, 2H).

$^{13}$C NMR (C$_6$D$_6$, 125 MHz): δ=296.9, 296.6, 265.0, 153.4, 150.9, 146.3, 144.9, 144.5, 144.3, 143.7, 139.7, 130.9, 130.1, 129.7, 129.5, 128.0, 127.7, 127.3, 124.0, 122.2, 113.8, 78.0, 75.8, 75.1, 64.2, 63.8, 58.3, 49.3, 31.2, 30.3, 29.8, 28.1, 27.5, 26.4, 25.9, 25.0, 22.7, 22.6, 16.3, 15.7, 15.0.

HRMS: ESI was calculated for C$_{33}$H$_{41}$NClORu [M−Cl]$^+$: 604.1920. found: 604.1917.

Elemental analysis: calculated for C$_{33}$H$_{41}$NCl$_2$ORu: C, 61.96; H, 6.46; N, 2.19; Cl, 11.08. found: C, 61.93; H, 6.59; N, 2.14; Cl, 11.23.

Example XIX

Reaction for Preparing Complex 2af

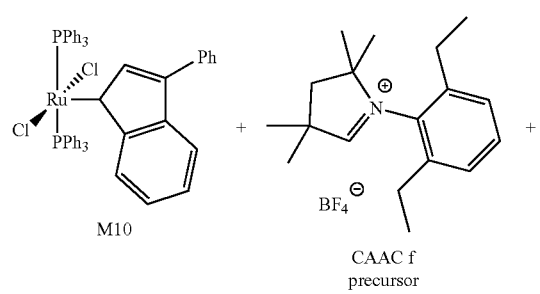

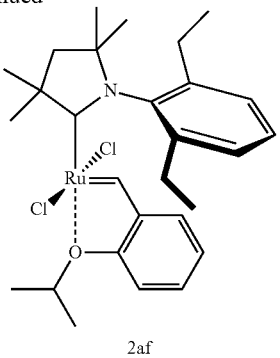

To CAAC f precursor (1.73 g, 5.0 mmol, 2 molar eq.) dry deoxygenated toluene (20 ml) was added under argon. The mixture was heated to 80° C. and a solution of LiHMDS in toluene (1 M, 5.0 ml, 5.0 mmol, 2 molar eq.) was added. After 1 minute, a solid M10 complex (2.22 g, 2.5 mmol, 1 molar eq.) was added. After 2 minutes the mixture was cooled to 60° C. Benzylidene ligand a (0.529 g, 3.0 mmol, 1.2 molar eq.) and CuCl (0.866 g, 8.75 mmol, 3.5 molar eq.) were added. The mixture was stirred for 5 minutes at 60° C. and cooled to room temperature. The crude product was isolated by column chromatography on silica gel (eluent: toluene). The green fraction was collected and concentrated to dryness. The residue was dissolved in ethyl acetate and filtered. The solvent was evaporated, and the residue was washed with isopropanol and dried under highly reduced pressure to give a green crystalline solid—the 2af precatalyst (0.584 g, 40%).

$^1$H NMR (C$_6$D$_6$, 500 MHz): δ=16.41 (s, 1H), 7.33 (dd, J=9.1; 2.7 Hz, 1H), 7.01 (d, J=1.6 Hz, 1H), 6.64 (s, 2H), 7.08 (d, J=9.1 Hz, 1H), 4.67 (septet, J=6.1 Hz, 1H), 2.87 (s, 3H), 2.45 (s, 2H), 2.23 (s, 6H), 1.77 (s, 6H), 1.70 (d, J=6.1 Hz, 6H), 0.97 (s, 6H).

Example XX

Reaction for preparing complex 2bg

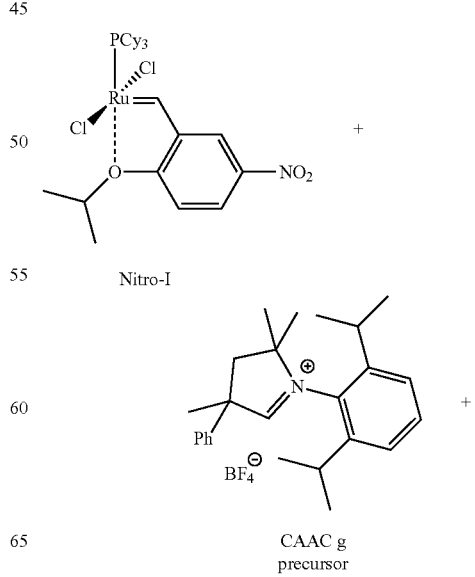

To CAAC g precursor (0.348 g, 0.8 mmol, 2 molar eq.) dry deoxygenated toluene (3.2 ml) was added under argon. The mixture was heated to 80° C. and a solution of LiHMDS in toluene (1 M, 0.8 ml, 0.8 mmol, 2 molar eq.) was added. After 1 minute, a solid Nitro-I complex (0.258 g, 0.4 mmol, 1 molar eq.) was added. The mixture was stirred for 15 minutes at 80° C. and cooled to room temperature. The crude product was isolated by column chromatography on silica gel (eluent: toluene). The green fraction was collected and concentrated to dryness. The residue was dissolved in ethyl acetate and filtered. The solvent was evaporated, and the residue was dissolved in methylene chloride and excess isopropanol was added. Methylene chloride was dried under vacuum—the crystals obtained were washed with a minimal volume of isopropanol, and then dried under highly reduced pressure to give a green crystalline solid—the 2bg precatalyst (0.037 g, 13%).

$^1$H NMR (CD$_2$Cl$_2$, 500 MHz): δ=16.49 (s, 1H), 8.40 (dd, J=9.1; 2.7 Hz, 1H), 8.24-8.20 (m, 2H), 7.74 (t, J=7.8 Hz, 1H), 7.59-7.49 (m 5H), 7.40-7.35 (m, 1H), 7.00 (d, J=9.1 Hz, 1H), 5.05 (septet, J=6.1 Hz, 1H), 3.15 (d, J=12.9 Hz, 1H), 3.04 (septet, J=6.6 Hz, 1H), 2.93 (septet, J=6.5 Hz, 1H), 2.38 (d, J=12.8 Hz, 1H), 2.33 (s, 3H), 1.57 (d, J=6.1 Hz, 3H), 1.53 (s, 3H), 1.43-1.40 (m, 6H), 1.36 (d, J=6.6 Hz, 3H), 1.27 (d, J=6.6 Hz, 3H), 0.80 (d, J=6.5 Hz, 3H), 0.48 (d, J=6.4 Hz, 3H).

$^{13}$C NMR (CD$_2$Cl$_2$, 125 MHz): δ=291.8, 291.4, 262.2, 157.4, 148.8, 148.5, 143.2 (2C), 142.9, 137.0, 130.5, 129.8, 129.6, 128.0, 126.8, 126.6, 125.9, 118.6, 113.9, 78.7, 77.9, 63.6, 48.6, 33.0, 29.4, 29.0, 28.8, 28.1, 27.5, 26.5, 24.7, 24.6, 22.7, 22.6.

HRMS: ESI was calculated for C$_{35}$H$_{44}$N$_2$O$_3$NaCl$_2$Ru [M+Na]$^+$: 735.1670. found: 735.1639.

Elemental analysis: calculated for C6H12N2Cl2O3Ru: C, 60.47; H, 6.68; N, 3.71; Cl, 9.39. found: C, 60.20; H, 6.52; N, 3.77; Cl, 9.48.

Example XXI

Reaction for Preparing Complex 2bh

To CAAC h precursor (1.87 g, 5.0 mmol, 2 molar eq.) dry deoxygenated toluene (20 ml) was added under argon. The mixture was heated to 80° C. and a solution of LiHMDS in toluene (1 M, 5.0 ml, 5.0 mmol, 2 molar eq.) was added. After 1 minute, a solid M10 complex (2.22 g, 2.5 mmol, 1 molar eq.) was added. After 2 minutes benzylidene ligand b (0.664 g, 3.0 mmol, 1.2 molar eq.) and CuCl (0.866 g, 8.75 mmol, 3.5 molar eq.) were added. The mixture was stirred for 15 minutes at 80° C. and cooled to room temperature. The crude product was isolated by column chromatography on silica gel (eluent: toluene). The green fraction was collected and concentrated to dryness. The residue was dissolved in ethyl acetate and filtered. The solvent was evaporated, and the residue was dissolved in methylene chloride and excess isopropanol was added. Methylene chloride was dried under vacuum—the crystals obtained were washed with a minimal volume of isopropanol, and then dried under highly reduced pressure to give a green crystalline solid—the 2bh precatalyst (0.490 g, 30%).

¹H NMR (CD₂Cl₂, 500 MHz): δ=16.31 (s, 1H), 8.42 (dd, J=9.1; 2.7 Hz, 1H), 7.73 (d, J=2.7 Hz, 1H), 7.52 (s, 2H), 7.09 (d, J=9.1 Hz, 1H), 5.27 (septet, J=6.2 Hz, 1H), 2.96 (s, 3H), 2.20 (s, 2H), 2.09 (s, 6H), 1.79 (s, 6H), 1.28 (d, J=6.7 Hz, 6H), 0.66 (s, 6H).

¹³C NMR (CD₂Cl₂, 125 MHz): δ=288.0, 287.7, 264.8, 157.5, 148.7, 143.3, 142.7, (2C), 136.7, 130.4, 126.5, 125.7, 118.3, 113.8, 79.1, 78.3, 56.7, 51.9, 30.2, 29.5, 29.0, 27.8, 25.7, 24.6, 22.4.

HRMS: ESI was calculated for C₃₀H₄₂N₂O₃ClRu [M−Cl]⁺: 615.1927. found: 615.1918.

Elemental analysis: calculated for C₃₀H₄₂N₂Cl₂O₃Ru: C, 55.38; H, 6.51; N, 4.31; Cl, 10.90. found: C, 55.15; H, 6.45; N, 4.15; Cl, 10.86.

Example XXII

Reaction for preparing complex 2ba

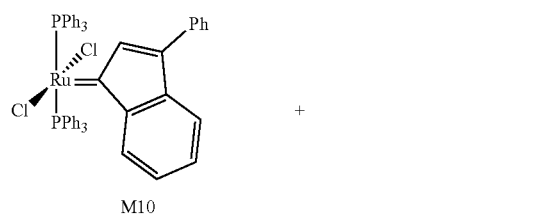

M10

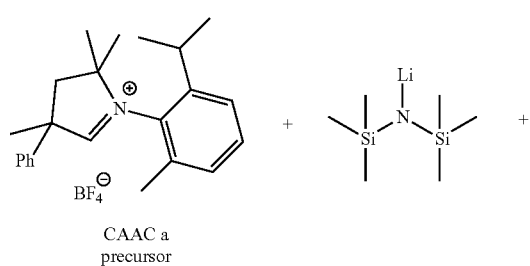

CAAC a precursor

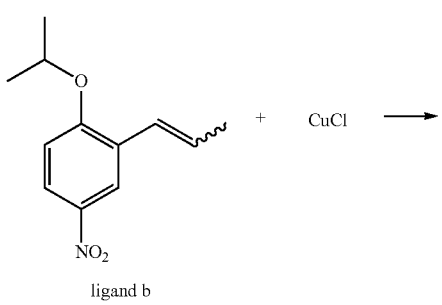

ligand b

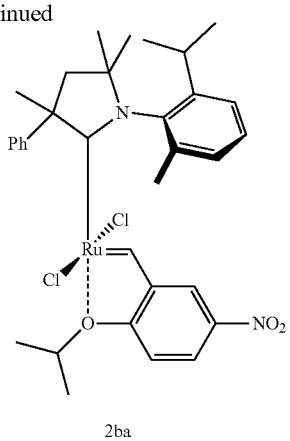

2ba

To CAAC a precursor (0.815 g, 2.0 mmol, 2 molar eq.) dry deoxygenated toluene (8 ml) was added under argon. The mixture was heated to 80° C. and a solution of LiHMDS in toluene (1 M, 2.0 ml, 2.0 mmol, 2 molar eq.) was added. After 1 minute, a solid M10 complex (0.887 g, 1.0 mmol, 1 molar eq.) was added. After 2 minutes benzylidene ligand b (0.266 g, 1.2 mmol, 1.2 molar eq.) and CuCl (0.346 g, 3.50 mmol, 3.5 molar eq.) were added. The mixture was stirred for 15 minutes at 80° C. and cooled to room temperature. The crude product was isolated by column chromatography on silica gel (eluent: toluene). The green fraction was collected and concentrated to dryness. The residue was dissolved in ethyl acetate and filtered. The solvent was evaporated, and the residue was washed with ethyl acetate-cyclohexane mixture 5:95. This was dissolved in methylene chloride and excess methanol was added. Methylene chloride was dried under vacuum—the crystals obtained were washed with a minimal volume of methanol, and then dried under highly reduced pressure to give a green crystalline solid—the 2ba precatalyst (0.235 g, 34%).

Mixture of Isomers.

¹H NMR (C₆D₆, 500 MHz): δ=[16.29 (br. s), 16.25 (s), 1H], 8.35-8.15 (m, 2H), 7.87 (dd, J=9.1; 2.8 Hz, 1H), 7.77 (dd, J=19.6; 2.7 Hz, 1H), 7.52 (t, J=7.9 Hz, 1H), 7.45 (t, J=7.6 Hz, 1H), 7.35-7.20 (m, 2H), 7.08-6.88 (m, 2H), 5.98 (d, J=9.1 Hz, 1H), 4.35 (ddt, J=15.9; 12.3; 6.1 Hz, 1H), 3.09 (septet, J=6.9 Hz, 1H), 2.88-2.67 (m, 1H), 2.52-2.28 (m, 5H), 2.22 (s, 2H), 1.93-1.86 (m, 1H), 1.48-1.33 (m, 3H), 1.32-1.20 (m, 4H), 1.19-0.97 (m, 10H).

¹³C NMR (C₆D₆, 125 MHz): δ=292.6, 291.6, 262.9, 157.0, 149.5, 149.3, 144.0, 143.6, 143.3, 142.3, 138.9, 138.8 (2C), 138.6, 132.8, 132.7, 132.0, 130.7, 130.5 (2C), 130.1 (2C), 129.9, 129.6 (2C), 129.3, 129.0, 128.9, 128.0, 127.9, 126.9, 126.4, 125.7, 125.5, 118.6, 118.4, 113.5, 78.4, 78.3, 77.4, 77.3, 64.2, 64.0, 63.5, 49.9, 49.1, 31.8, 31.4, 29.3, 28.8, 28.6, 28.4, 27.5, 27.4, 27.3, 26.2, 25.9, 24.5, 23.1, 22.5, 22.3, 21.9.

LRMS: ESI was calculated for C₃₃H₄₀N₂O₃ClRu [M−Cl]⁺: 649.18. found: 649.18.

Elemental analysis: calculated for solvate with 0.5 of isopropanol particle [M+0.5C₃H₈O]C₃H₈N₂Cl₂O₃.₅Ru: C, 57.98; H, 6.21; N, 3.92; Cl, 9.92. found: C, 58.08; H, 6.04; N, 3.89; Cl, 10.12.

Example XXIII

Reaction for Preparing Complex 2bb

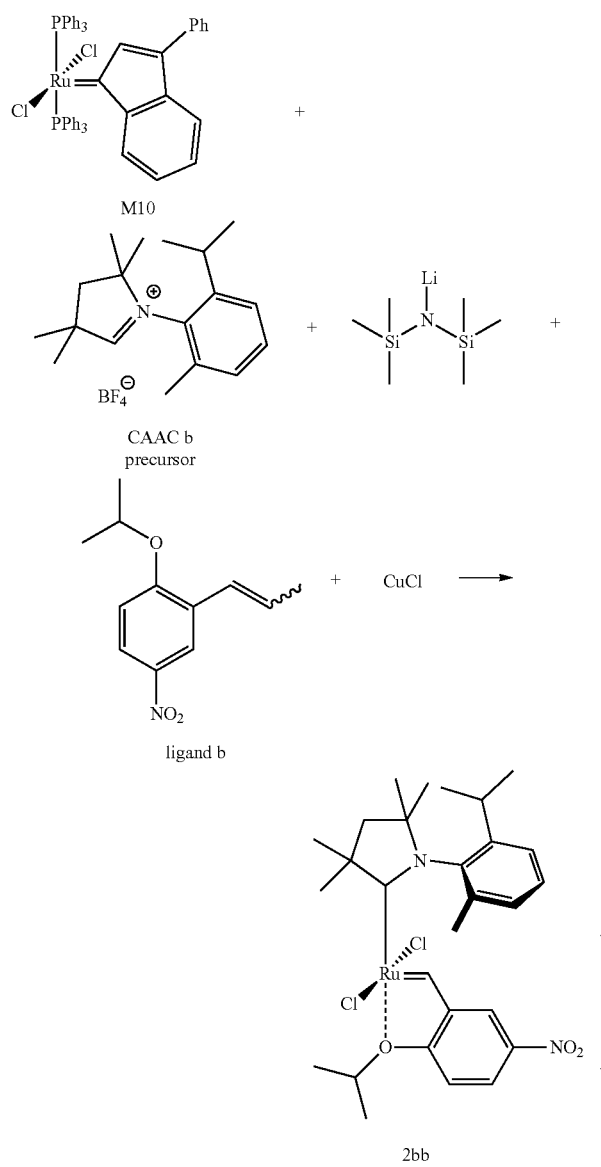

To CAAC b precursor (1.73 g, 5.0 mmol, 2 molar eq.) dry deoxygenated toluene (20 ml) was added under argon. The mixture was heated to 80° C. and a solution of LiHMDS in toluene (1 M, 5.0 ml, 5.0 mmol, 2 molar eq.) was added. After 1 minute, a solid M10 complex (2.22 g, 2.5 mmol, 1 molar eq.) was added. After 2 minutes the mixture was cooled to 60° C. Benzylidene ligand b (0.664 g, 3.0 mmol, 1.2 molar eq.) and CuCl (0.866 g, 8.75 mmol, 3.5 molar eq.) were added. The mixture was stirred for 5 minutes at 60° C. and cooled to room temperature. The crude product was isolated by column chromatography on silica gel (eluent: toluene). The green fraction was collected and concentrated to dryness. The residue was dissolved in ethyl acetate and filtered. The solvent was evaporated, and the residue was washed with isopropanol and dried under highly reduced pressure to give a green crystalline solid—the 2bb precatalyst (0.663 g, 42%).

$^1$H NMR (CD$_2$Cl$_2$, 500 MHz): δ=16.19 (s, 1H), 8.45 (dd, J=9.1; 2.7 Hz, 1H), 7.70 (d, J=2.7 Hz, 1H), 7.65 (t, J=7.7 Hz, 1H), 7.55 (dd, J=8.0; 1.5 Hz, 1H), 7.35 (ddd, J=7.5; 1.6; 0.7 Hz, 1H), 7.08 (d, J=8.9 Hz, 1H), 5.26 (sept, J=6.2 Hz, 1H), 2.97 (sept, J=6.7 Hz, 1H), 2.26-2.19 (m, 5H), 2.13 (s, 3H), 2.03 (s, 3H), 1.77 (dd, J=16.1; 6.1 Hz, 6H), 1.43 (s, 3H), 1.38 (s, 3H), 1.30 (d, J=6.6 Hz, 3H), 0.68 (d, J=6.5 Hz, 3H).

$^{13}$C NMR (CD$_2$Cl$_2$, 125 MHz): δ=290.2, 264.6, 157.2, 149.1, 143.5, 143.4, 138.5, 138.4, 130.4, 130.0, 126.5, 125.8, 118.4, 113.7, 79.4, 78.2, 56.6, 52.3, 29.9, 29.7, 29.6, 29.1, 28.9, 26.3, 24.3, 22.4, 22.3, 21.8.

HRMS: ESI was calculated for C$_{28}$H$_{38}$ClN$_2$O$_3$Ru [M−Cl]$^+$: 587.1613. found: 587.1636.

Elemental analysis: calculated for C$_{28}$H$_{38}$N$_2$Cl$_2$O$_3$Ru: C, 54.02; H, 6.15; N, 4.50; Cl, 11.39. found: C, 54.19; H, 6.18; N, 4.37; Cl, 11.21.

Example XXIV

Reaction for Preparing Complex 2ab

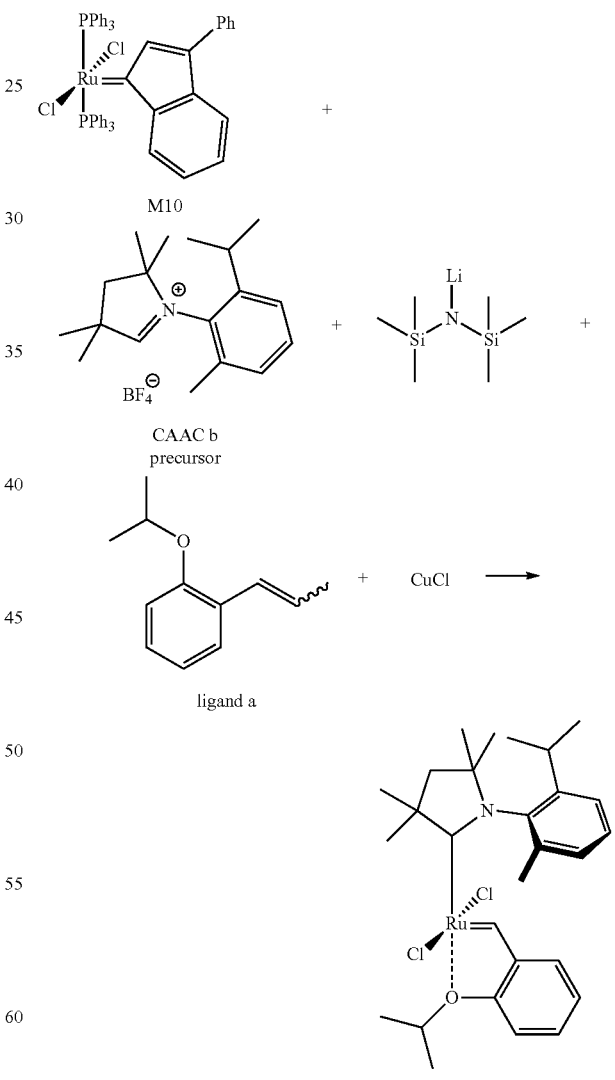

To CAAC b precursor (1.73 g, 5.0 mmol, 2 molar eq.) dry deoxygenated toluene (20 ml) was added under argon. The mixture was heated to 80° C. and a solution of LiHMDS in toluene (1 M, 5.0 ml, 5.0 mmol, 2 molar eq.) was added. After 1 minute, a solid M10 complex (2.22 g, 2.5 mmol, 1 molar eq.) was added. After 2 minutes the mixture was cooled to 60° C. Benzylidene ligand a (0.529 g, 3.0 mmol, 1.2 molar eq.) and CuCl (0.866 g, 8.75 mmol, 3.5 molar eq.) were added. The mixture was stirred for 5 minutes at 60° C. and cooled to room temperature. The crude product was isolated by column chromatography on silica gel (eluent: toluene). The green fraction was collected and concentrated to dryness. The residue was dissolved in ethyl acetate and filtered. The solvent was evaporated, and the residue was washed with isopropanol and dried under highly reduced pressure to give a green crystalline solid—the 2ab precatalyst (0.688 g, 47%).

$^1$H NMR (CD$_2$Cl$_2$, 500 MHz): δ=16.20 (s, 1H), 7.60-7.53 (m, 2H), 7.50-7.47 (m, 1H), 7.29 (ddd, J=7.4; 1.7; 0.8 Hz, 1H), 6.97 (d, J=8.3 Hz, 1H), 6.92-6.85 (m, 2H), 5.16 (sept, J=6.1 Hz, 1H), 2.98 (sept, J=6.6 Hz, 1H), 2.24 (s, 3H), 2.23-2.16 (m, 2H), 2.13 (s, 3H), 2.02 (s, 3H), 1.75 (d, J=6.1 Hz, 3H), 1.71 (d, J=6.1 Hz, 3H), 1.40 (s, 3H), 1.36 (s, 3H), 1.28 (d, J=6.7 Hz, 3H), 0.67 (d, J=6.5 Hz, 3H).

Example XXV

Reaction for Preparing Complex 2cb

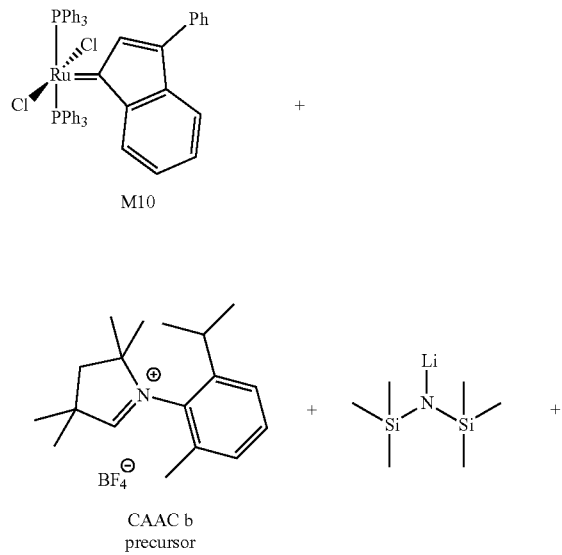

M10

CAAC b precursor

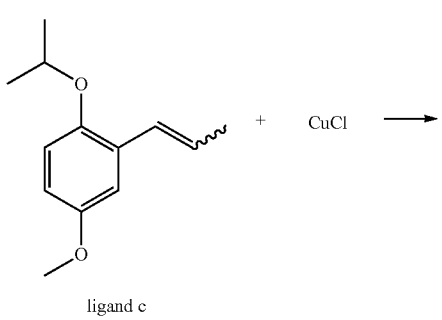

ligand c

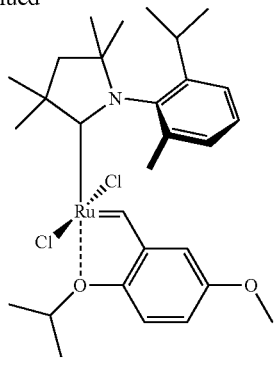

2cb

To CAAC b precursor (1.56 g, 4.51 mmol, 2 molar eq.) dry deoxygenated toluene (18 ml) was added under argon. The mixture was heated to 60° C. and a solution of LiHMDS in toluene (1 M, 4.51 ml, 4.51 mmol, 2 molar eq.) was added. After 1 minute, a solid M10 complex (2.00 g, 2.26 mmol, 1 molar eq.) was added. After 2 minutes benzylidene ligand c (0.558 g, 2.71 mmol, 1.2 molar eq.) and CuCl (0.781 g, 7.89 mmol, 3.5 molar eq.) was added. The mixture was stirred for 5 minutes at 60° C. and cooled to room temperature. The crude product was isolated by column chromatography on silica gel (eluent: toluene). The green fraction was collected and concentrated to dryness. The residue was dissolved in ethyl acetate and filtered. The solvent was evaporated, and the residue was washed with isopropanol and dried under highly reduced pressure to give a green crystalline solid—the 2cb precatalyst (0.741 g, 54%).

$^1$H NMR (C$_6$D$_6$, 500 MHz): δ=16.24 (s, 1H), 7.21-7.17 (m, 2H), 7.00-6.95 (m, 1H), 6.83 (dd, J=8.9; 3.0 Hz, 1H), 6.65 (d, J=3.0 Hz, 1H), 6.38 (dd, J=9.6; 1.0 Hz, 1H), 4.67 (septet, J=6.1 Hz, 1H), 3.35 (s, 1H), 3.14 (septet, J=6.6 Hz, 1H), 2.28 (d, J=3.6 Hz, 6H), 2.20 (s, 3H), 1.83-1.71 (m, 8H), 1.13 (d, J=6.7 Hz, 3H), 1.03 (s, 3H), 0.94 (s, 3H), 0.91 (d, J=6.5 Hz, 3H).

$^{13}$C NMR (CD$_2$Cl$_2$, 125 MHz): δ=292.3, 268.5, 155.5, 149.7, 147.7, 144.8, 139.2, 139.1, 130.1, 129.4, 128.9, 127.9, 126.3, 115.5, 113.8, 109.0, 78.1, 75.2, 56.8, 55.9, 52.1, 29.9, 29.8, 29.7, 29.0, 28.8, 26.9, 25.9, 24.5, 22.5 (2C), 22.1.

HRMS: ESI was calculated for C$_{29}$H$_{41}$NO$_3$ClRu [M−Cl]$^+$: 572.1869. found: 572.1870.

Elemental analysis: calculated for C$_{29}$H$_{41}$NCl$_2$O$_3$Ru: C, 57.32; H, 6.80; N, 2.31; Cl, 11.67. found: C, 57.10; H, 6.71; N, 2.36; Cl, 11.62.

Example XXVI

Reaction for Preparing Complex nG-diEt

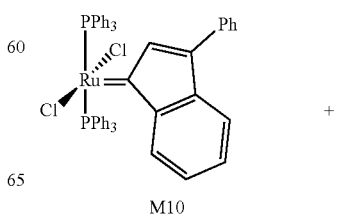

M10

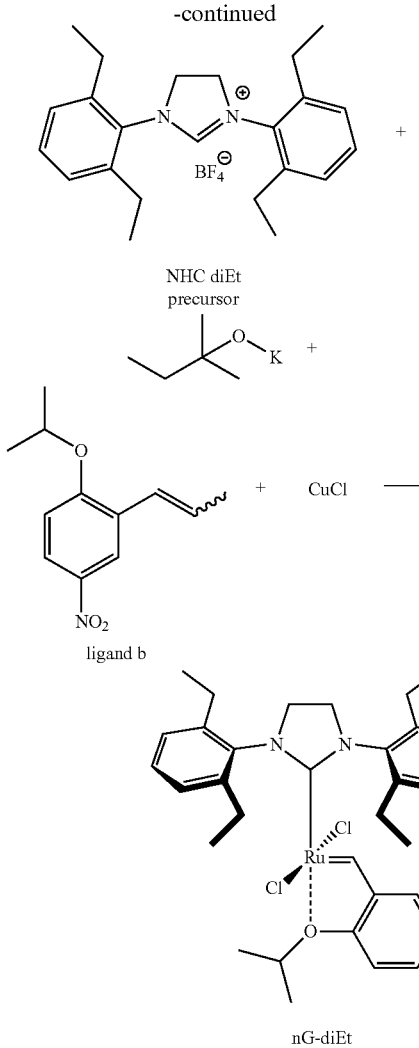

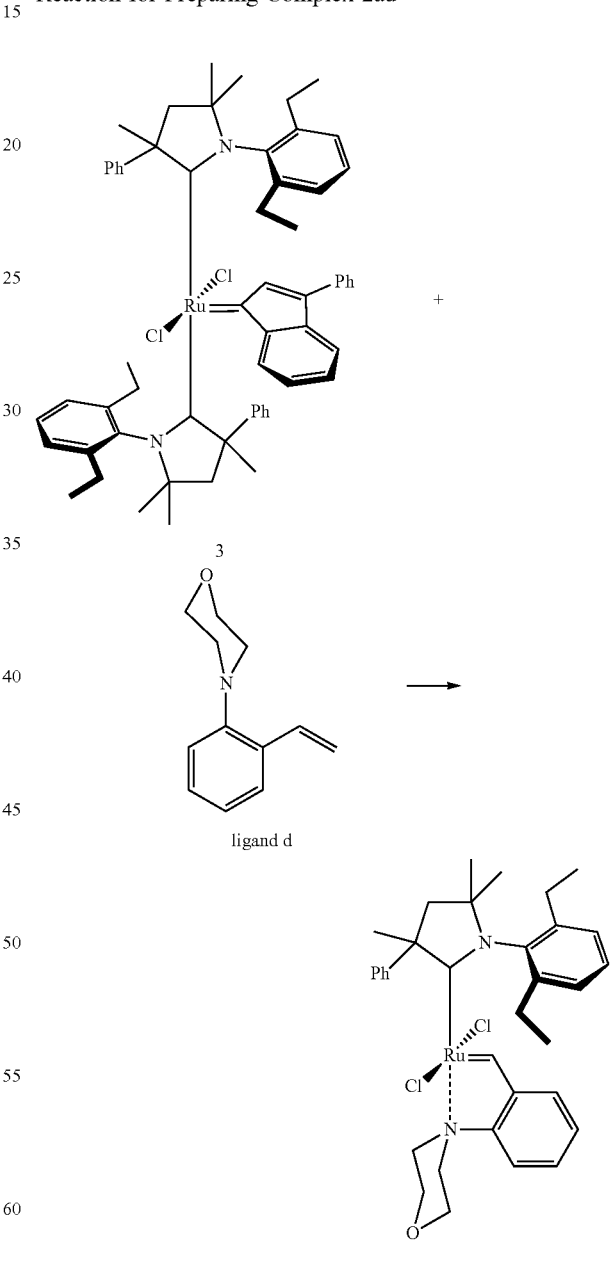

To NHC diEt precursor (5.00 g, 11.84 mmol, 1.18 molar eq.) dry deoxygenated toluene (93 ml) was added under argon. The mixture was heated to 80° C. and a solution of potassium tert-amylate in toluene (1.7 M, 5.0 ml, 5.0 mmol, 1.15 molar eq.) was added. After 10 minutes, a solid M10 complex (8.90 g, 10.03 mmol, 1 molar eq.) was added. After 10 minutes the mixture was cooled to 50° C. Benzylidene ligand b (2.66 g, 12.04 mmol, 1.2 molar eq.) and CuCl (2.48 g, 25.08 mmol, 2.5 molar eq.) were added. The mixture was stirred for 20 minutes at 50° C. and cooled to room temperature. The crude product was isolated by column chromatography on silica gel (eluent: ethyl acetate-cyclohexane 1:9). The green fraction was collected and concentrated to dryness. The residue was dissolved in ethyl acetate and filtered. The solvent was evaporated, and the residue was dissolved in methylene chloride and excess methanol was added. The methylene chloride was slowly removed under reduced pressure—the resulting crystals were filtered off and washed in a minimum volume of methanol. This was dried under highly reduced pressure to give a green crystalline solid—the nG-diEt precatalyst (2.20 g, 31%).

$^1$H NMR (CD$_2$Cl$_2$, 500 MHz): δ=16.32 (s, 1H), 8.41 (dd, J=9.1; 2.7 Hz, 1H), 7.76 (d, J=2.8 Hz, 1H), 7.58-7.50 (m, 2H), 7.38-7.32 (m, 4H), 6.92 (d, J=9.1 Hz, 1H), 4.96 (septet, J=6.1 Hz, 1H), 4.22 (s, 4H), 3.05-2.90 (br. s, 4H), 2.84 (dq, J=15.1; 7.5 Hz, 4H), 1.28-1.22 (m, 18H).

$^{13}$C NMR (CD$_2$Cl$_2$, 125 MHz): δ=287.0, 209.0, 161.0, 157.0, 145.3, 144.9, 143.7, 141.6, 137.5, 132.5, 132.4 (2C), 130.1, 129.9, 129.1, 129.0, 128.2, 127.3, 127.1, 126.8, 125.6, 125.1, 124.7, 123.4, 117.1, 113.4, 113.0, 78.4, 72.4, 25.5, 22.3, 21.6, 15.2.

HRMS: ESI was calculated for C$_{33}$H$_{41}$N$_3$O$_3$ClRu [M−Cl]$^+$: 664.1880. found: 664.1876.

Elemental analysis: calculated for C$_{33}$H$_{41}$N$_3$Cl$_2$O$_3$Ru: C, 56.65; H, 5.91; N, 6.01; Cl, 10.13. found: C, 56.47; H, 5.76; N, 5.84; Cl, 10.04.

Example XXVII

Reaction for Preparing Complex 2ad

To complex 3 (2.00 g, 2.0 mmol, 1 molar eq.) dry deoxygenated toluene (20 ml) and benzylidene ligand d (0.568 g, 3.0 mmol, 1.5 molar eq.) were added under argon.

The mixture was stirred for 20 minutes at 80° C. and cooled to room temperature. The crude product was isolated by column chromatography on silica gel (toluene→ethyl acetate/cyclohexane 2:8). The green fraction was collected and concentrated to dryness. The residue was dissolved in methylene chloride and excess methanol was added. The methylene chloride was slowly removed under reduced pressure. The resulting precipitate was filtered off and washed with cold methanol to give a green crystalline solid—the 2dd precatalyst (0.750 g, 56%).

$^1$H NMR (CD$_2$Cl$_2$, 500 MHz): δ=16.97 (s, 1H), 8.40 (dd, J=8.3; 1.4 Hz, 2H), 7.67-7.57 (m, 4H), 7.50-7.46 (m, 1H), 7.46-7.38 (m, 3H), 7.17-7.12 (m, 1H), 6.71 (dd, J=7.7; 1.6 Hz, 1H), 4.30 (ddd, J=12.3; 11.3; 2.0 Hz, 1H), 3.89 (ddt, J=12.1; 2.8; 1.4 Hz, 1H), 3.68 (dd, J=11.2; 2.1 Hz, 1H), 3.52-3.45 (m, 1H), 3.45-3.39 (m, 1H), 3.23 (dd, J=11.2; 2.1 Hz, 1H), 3.16 (d, J=12.5 Hz, 1H), 2.92 (td, J=11.2; 3.1 Hz, 1H), 2.85-2.75 (m, 2H), 2.72-2.58 (m, 2H), 2.49 (dq, J=14.9; 7.4 Hz, 1H), 2.33 (d, J=12.5 Hz, 1H), 2.30 (s, 3H), 1.52 (s, 3H), 1.40 (s, 3H), 1.08 (t, J=7.4 Hz, 3H), 0.75 (t, J=7.4 Hz, 3H).

$^{13}$C NMR (CD$_2$Cl$_2$, 125 MHz): δ=307.0, 263.6, 153.4, 149.2, 146.1, 143.9, 143.6, 139.1, 130.4, 130.1, 129.5, 129.4, 128.1, 127.9, 127.6, 127.1, 124.9, 123.0, 79.0, 67.3, 67.2, 65.0, 56.1, 55.7, 46.8, 31.6, 29.4, 27.4, 26.2, 24.5, 15.3, 14.5.

HRMS: ESI was calculated for C$_{34}$H$_{42}$N$_2$ONaCl$_2$Ru [M+Na]$^+$: 689.1615. found: 689.1595.

Elemental analysis: calculated for C$_{34}$H$_{42}$N$_2$OCl$_2$Ru: C, 61.25; H, 6.35; N, 4.20; Cl, 10.64. found: C, 61.12; H, 6.37; N, 4.21; Cl, 10.80.

Example XXVIII

Reaction for Preparing Complex 2ed

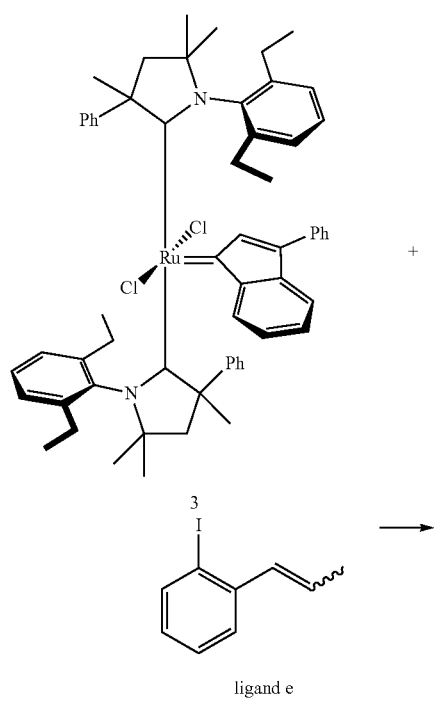

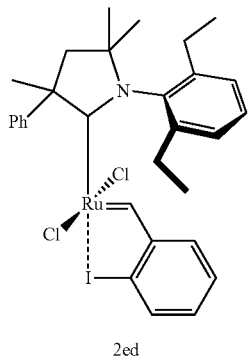

To the suspension of complex 3 (1.00 g, 1.0 mmol, 1 molar eq.) in dry deoxygenated dioxane (10 ml) benzylidene ligand e (0.488 g, 2.0 mmol, 2 molar eq.) was added under argon. The mixture was stirred for 30 minutes at 80° C. and cooled to room temperature. This was filtered off and washed with dioxane. A green crystalline solid was obtained—the precatalyst 2ed (0.585 g, 83%).

$^1$H NMR (CD$_2$Cl$_2$, 500 MHz): δ=17.40 (s, 1H), 8.26-8.21 (m, 2H), 7.58-7.52 (m, 2H), 7.44-7.39 (m, 2H), 7.36-7.33 (m, 1H), 7.26 (td, J=7.5; 1.6 Hz, 1H), 7.18 (td, J=7.4; 1.0 Hz, 1H), 7.07 (t, J=7.7 Hz, 1H), 6.80 (dd, J=7.6; 1.6 Hz, 1H), 6.33 (d, J=7.7 Hz, 1H), 3.26 (dq, J=15.1; 7.4 Hz, 1H), 2.97 (d, J=13.4 Hz, 1H), 2.66 (s, 3H), 2.57 (dq, J=15.0; 7.3 Hz, 1H), 2.38 (d, J=13.4 Hz, 1H), 2.02 (dq, J=14.7; 7.3 Hz, 1H), 1.62 (dq, J=15.0; 7.5 Hz, 1H), 1.51 (s, 3H), 1.42 (t, J=7.4 Hz, 3H), 1.26 (s, 3H), 0.90 (t, J=7.4 Hz, 3H).

$^{13}$C NMR (CD$_2$Cl$_2$, 125 MHz): δ=282.9, 282.8, 267.5, 158.3, 145.5, 142.7, 141.3, 136.9, 134.4, 131.7, 131.2, 129.5, 129.3, 128.8, 127.1, 126.7, 126.1, 102.2, 80.3, 62.4, 50.2, 30.8, 30.2, 29.0, 25.8, 25.6, 15.2, 14.1.

HRMS: ESI was calculated for C$_{30}$H$_{34}$NClRuI [M–Cl]$^+$: 672.0468. found: 672.0455.

Elemental analysis: calculated for C$_{30}$H$_{34}$NCl$_2$IRu: C, 50.93; H, 4.84; N, 1.98; Cl, 10.02; I, 17.94. found: C, 51.01; H, 4.98; N, 2.03; Cl, 10.01; I, 17.71.

Example XIX

RCM Reaction of Diethyl Diallylmalonate (S3)

To a solution of S3 (0.240 g, 1.0 mmol) in toluene (10 ml) at 29° C. or 40° C. or 80° C., the precatalyst solution (0.1 mol %) in toluene (50 μl) was added in one portion. At required intervals, samples were taken of the reaction mixture to which a few drops of ethyl vinyl ether were added to deactivate the catalyst. The samples were analysed by gas chromatography.

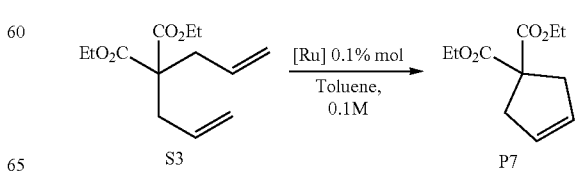

TABLE 14

Experimental results of the CM reaction of methyl acrylate with S1

| Time [min] | Conversion [%] | | |
|---|---|---|---|
| | 29° C. 2ed | 40° C. 2dd | 80° C. 2dd |
| 2.5 | 58 | — | 4 |
| 5 | 89 | — | 10 |
| 10 | 99 | 0.5 | 28 |
| 20 | 99.5 | — | 62 |
| 30 | — | — | 78 |
| 45 | — | — | 85 |
| 60 | — | 2.3 | 88 |

Metathesis Products Analytical Data

P1:

main isomer, E: $^1$H NMR (CDCl$_3$, 500 MHz): δ=6.95 (dt, J=15.7; 7.0 Hz, 1H), 5.83-5.77 (dt, J=15.6; 1.6 Hz, 1H) 5.80 (dt, J=15.6; 1.6 Hz, 1H), 4.10 (q, J=7.2 Hz, 2H), 3.71 (s, 3H), 2.26 (t, J=7.5 Hz, 2H), 2.17 (qd, J=7.1; 1.6 Hz, 2H), 1.64-1.54 (m, 2H), 1.47-1.38 (m, 2H), 1.33-1.25 (m, 8H), 1.23 (t, J=7.1 Hz, 3H).

$^{13}$C NMR (CDCl$_3$, 125 MHz): δ=173.8, 167.1, 149.7, 120.8, 60.1, 51.3, 34.3, 32.1, 29.1, 29.1, 29.0, 29.0, 27.9, 24.9, 14.1)

P2:

main isomer, Z: $^1$H NMR (CDCl$_3$, 500 MHz): δ=6.46 (s, 1H), 8.48 (dd, J=10.9; 7.7 Hz, 1H), 5.29 (d, J=2.8 Hz, 1H), 7.20 (s, 2H), 4.10 (d, J=7.1 Hz, 1H), 2.40 (septet, J=1.4 Hz, 1H), 2.26 (s, 3H), 1.64 (s, 2H), 1.49 (s, 6H), 1.35 (s, 6H), 1.23 (d, J=7.1 Hz, 6H), 1.43 (s, 6H).

$^{13}$C NMR (CDCl$_3$, 125 MHz): δ=173.8, 156.0 (E), 155.1 (Z), 117.5 (E), 116.0 (Z), 99.6 (E), 99.4 (Z), 60.1 (2C, E+Z), 34.3 (Z), 34.2 (E), 33.2 (E), 31.8 (E), 29.0 (6C, E+Z), 28.9 (Z), 28.8 (E), 28.1 (2), 27.5 (E), 24.9 (Z), 24.8 (E), 14.2.

P3:

main isomer, Z: $^1$H NMR (CDCl$_3$, 500 MHz): δ=6.46 (dt, J=10.9; 7.7 Hz, 1H), 5.29 (dt, J=10.9; 1.3 Hz, 1H), 3.65 (s, 3H), 2.40 (dq, J=7.6; 1.3 Hz, 2H), 2.29 (t, J=7.5 Hz, 2H), 1.64-1.54 (m, 2H), 1.50-1.39 (m, 2H), 1.36-1.26 (m, 6H).

$^{13}$C NMR (CDCl$_3$, 125 MHz): δ=174.12 (Z), 174.08 (E), 156.0 (E), 155.0 (Z), 117.5 (E), 116.0 (Z), 99.6 (E), 99.5 (Z), 51.39 (E), 51.37 (Z), 33.95 (Z), 33.92 (E), 33.2 (E) 31.7 (Z), 28.87 (Z), 28.85 (E), 28.83 (Z+E), 28.72 (Z), 28.68 (E), 28.1 (2), 27.5 (E), 24.77 (Z), 24.75 (E).

P4:

main isomer, Z: $^1$H NMR (CDCl$_3$, 500 MHz): δ=6.47 (dt, J=10.9; 7.7 Hz, 1H), 5.29 (dt, J=11.0; 1.4 Hz, 1H), 2.41 (qd, J=7.5; 1.4 Hz, 2H), 1.50-1.38 (m, 2H), 1.37-1.21 (m, 10H), 0.87 (t, J=7.0 Hz, 3H).

$^{13}$C NMR (126 MHz, CDCl$_3$1: δ=156.1 (E), 155.2 (Z), 117.5 (E), 116.0 (Z), 99.6 (E), 99.4 (Z), 33.3 (E), 31.8 (E), 31.7, 29.2 (2C, Z+E), 29.1 (2C, Z+E), 29.0 (Z), 28.9 (E), 28.2 (Z), 27.6 (E), 22.6, 14.0.

P5:

$^1$H NMR (CDCl$_3$, 500 MHz): δ=5.79 (ddt, J=17.0; 10.2; 6.7 Hz, 1H), 4.98 (dq, J=17.1; 1.7 Hz, 1H), 4.92 (ddd, J=11.4; 2.3; 1.2 Hz, 1H), 3.66 (s, 3H), 2.29 (t, J=7.5 Hz, 2H), 2.06-1.99 (m, 2H), 1.66-1.56 (m, 2H), 1.40-1.24 (m, 8H).

$^{13}$C NMR (CDCl$_3$, 125 MHz): 174.3, 139.1, 114.2, 51.4, 34.1, 33.7, 29.1, 28.9, 28.8, 24.9.

D1:

$^1$H NMR (CDCl$_3$, 600 MHz): δ=5.41-5.30 (m, 2H), 4.14-4.08 (m, 4H), 2.30-2.24 (m, 4H), 2.02-1.90 (m, 4H), 1.64-1.56 (m, 4H), 1.35-1.21 (m, 26H).

$^{13}$C NMR (CDCl$_3$, 150 MHz): δ=173.8, 130.3, 60.1, 34.4, 32.5, 29.6, 29.3, 29.2, 29.1, 29.0, 24.9, 14.2.

D2:

$^1$H NMR (CDCl$_3$, 500 MHz): δ=5.36 (ddd, J=5.3; 3.7; 1.6 Hz, 2H, E), 5.32 (ddd, J=5.7; 4.3; 1.1 Hz, 2H, Z), 3.65 (s, 6H), 2.29 (t, J=7.5 Hz, 4H), 2.03-1.90 (m, 4H), 1.68-1.56 (m, 4H), 1.35-1.23 (m, 16H).

$^{13}$C NMR (CDCl$_3$, 125 MHz): δ=174.25 (E), 174.24 (Z), 130.3 (E), 129.8 (Z), 51.4, 34.1, 32.5, 29.6 (Z), 29.5 (E), 29.12 (Z), 29.08 (E), 29.07 (E), 29.05 (Z), 28.9, 27.1 (Z), 24.9 (E).

D3:

$^1$H NMR (CDCl$_3$, 500 MHz): δ=5.39 (ddd, J=5.3; 3.7; 1.6 Hz, 2H, E), 5.35 (ddd, J=5.7; 4.4; 1.1 Hz, 2H, Z), 2.06-1.91 (m, 4H), 1.38-1.18 (m, 24H), 0.88 (t, J=6.9 Hz, 6H).

$^{13}$C NMR (CDCl$_3$, 125 MHz): δ=130.4 (E), 129.9 (Z), 32.6, 31.9, 29.8 (Z), 29.7 (E), 29.53 (Z), 29.51 (E), 29.3, 29.2 (E), 27.2 (Z), 22.7, 14.1.

"The project leading to this application has received funding from the European Union's Horizon 2020 research and innovation programme under grant agreement No 635405".

The invention claimed is:

1. A method of performing an olefin metathesis reaction comprising contacting at least one type of acyclic olefin selected from the group consisting of ethyl undecanoate, 1-decene, acrylonitrile, methyl acrylate and methyl stearate with a compound of formula 2, wherein the compound of formula 2 is used in an amount of less than 0.1 mol %, wherein at least one compound is formed as the main product containing at least one non-terminal double C=C bond,

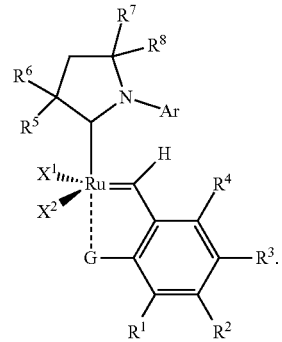

2 wherein:

$X^1$ and $X^2$ are each a halogen atom, —OR', —SR', —O(C=O)R', or —O(SO$_2$)R', wherein R' is $C_1$-$C_{12}$ alkyl, $C_3$-$C_{12}$ cycloalkyl, or $C_5$-$C_{20}$ aryl; $X^1$ and $X^2$ may be interconnected to form a cyclic system;

G is a halogen atom or a substituent selected from the group consisting of OR', SR', S(O)R', S(O)$_2$R' N(R')(R"), and P(R')(R")(R'"), where R', R" and R'" are the same or different $C_1$-$C_{25}$ alkyl group, $C_3$-$C_{12}$ cycloalkyl group, $C_1$-$C_{25}$ alkoxy group, $C_2$-$C_{25}$ alkenyl group, $C_1$-$C_{12}$ perfluoroalkyl, $C_5$-$C_{20}$ aryl, $C_5$-$C_{24}$ aryloxy, $C_2$-$C_{20}$ heterocyclyl, $C_4$-$C_{20}$, heteroaryl, $C_5$-$C_{20}$, or which may involve the formation of a substituted or non-substituted cyclic $C_4$-$C_{10}$ or policyclic $C_4$-$C_{12}$ systems, which are optionally substituted with at least one $C_1$-$C_{12}$ alkyl, $C_1$-$C_{12}$ perfluoroalkyl, $C_1$-$C_{12}$ alkoxy, $C_5$-$C_{24}$ aryloxy, $C_2$-$C_{20}$ heterocyclyl, $C_4$-$C_{20}$ heteroaryl, $C_5$-$C_{20}$ heteroaryloxy, may also be substituted with a (COOR') ester group, a (—CONR'$_2$) amide group, a (—CHO) formyl group, a (—COR') ketone group, or a (—CON(OR')(R')) hydroxamic group, wherein R' is $C_1$-$C_{12}$ alkyl, $C_3$-$C_{12}$ cycloalkyl, $C_2$-$C_{12}$ alkenyl, or $C_5$-$C_{20}$ aryl, which are optionally substituted with at least one $C_1$-$C_{12}$ alkyl, $C_1$-$C_{12}$ perfluoroalkyl, $C_1$-$C_{12}$ alkoxy, $C_5$-$C_{20}$ aryl, $C_5$-$C_{24}$ aryloxy, $C_7$-$C_{24}$ aralkyl, $C_2$-$C_{20}$ heterocycle, $C_4$-$C_{20}$, heteroaryl, $C_5$-$C_{20}$ heteroaryloxy, or a halogen atom;

Ar is an aryl group that is substituted by hydrogen atoms, or optionally is substituted by at least one $C_1$-$C_{12}$ alkyl, $C_1$-$C_{12}$ perfluoroalkyl, $C_1$-$C_{12}$ alkoxy, $C_5$-$C_{24}$ aryloxy, $C_2$-$C_{20}$ heterocyclic, $C_4$-$C_{20}$ heteroaryl, $C_5$-$C_{20}$ heteroaryloxy, $C_7$-$C_{24}$ aralkyl, $C_5$-$C_{24}$ perfluoroaryl, or a halogen atom;

$R^1$, $R^2$, $R^3$, $R^4$ are each a hydrogen atom, a (—S(O)R') sulphoxide group, a (—SO$_2$NR'$_2$) sulphonamide group, a (—P(O)(OR')$_2$) phosphonium group, a (—P(O)R' (OR')) phosphonium group, a (—P(OR')$_2$) phosphonous group, a (—PR'$_2$) phosphine group, a (—NO$_2$) nitro group, a (—NO) nitroso group, a (—COOH) carboxy group, a (—COOR') ester group, a (—CHO) formyl group, a (—COR') ketone group, a —NC(O)R' group, an amino group, an ammonium group, or a (—OMe) alkoxy group, wherein R' is $C_1$-$C_5$ alkyl, $C_1$-$C_5$ perfluoroalkyl, $C_5$-$C_{24}$ aryl, $C_7$-$C_{24}$ aralkyl, $C_5$-$C_{24}$ perfluoroaryl, $C_4$-$C_{20}$ heteroaryl, or $C_5$-$C_{20}$ heteroaryloxy, and wherein $R^1$, $R^2$, $R^3$ and $R^4$ may be interconnected to form a cyclic system;

$R^5$ and $R^6$ are each $C_1$-$C_{25}$ alkyl, $C_3$-$C_{12}$ cycloalkyl, $C_5$-$C_{20}$ aryl, $C_2$-$C_{20}$ heterocycle, $C_4$-$C_{20}$ heteroaryl, $C_7$-$C_{24}$ aralkyl, which are optionally substituted by at least one $C_1$-$C_{12}$ alkyl, $C_1$-$C_{12}$, perfluoroalkyl, $C_1$-$C_{12}$ alkoxy, $C_5$-$C_{24}$ aryloxy, $C_4$-$C_{20}$ heteroaryl, or $C_5$-$C_{20}$ heteroaryloxy, or a halogen atom; and wherein $R^5$ and $R^6$ may be interconnected to form a cyclic system; and $R^7$ and $R^8$ are each a hydrogen atom or a $C_1$-$C_{25}$ alkyl, or a $C_3$-$C_{12}$ cycloalkyl, and wherein $R^7$ and $R^8$ may be interconnected to form a cyclic system.

2. The method according to claim 1, wherein in formula 2

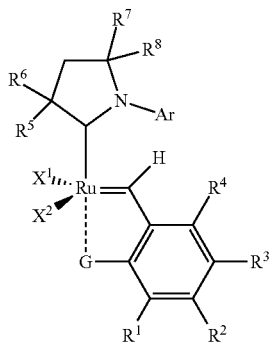

$X^1$ and $X^2$ are halogen atoms;

G is a halogen atom or a substituent selected from the group consisting of OR' and N(R')(R'') group, wherein R' and R'' are the same or different $C_1$-$C_{12}$ alkyl, $C_3$-$C_{12}$ cykloalkyl, $C_2$-$C_{12}$ alkenyl, or $C_5$-$C_{20}$ aryl, which are optionally substituted by at least one $C_1$-$C_{12}$ alkyl, $C_1$-$C_{12}$ perfluoroalkyl, $C_1$-$C_{12}$ alkoxy, $C_5$-$C_{24}$ aryloxy, or $C_5$-$C_{20}$ heteroaryloxy;

$R^1$, $R^2$, $R^3$, $R^4$ are each a hydrogen atom, a (—S(O)R') sulphoxide group, a (—SO$_2$NR'$_2$) sulphonamide group, a (—P(O)(OR')$_2$) phosphonium group, a (—P(O)R' (OR')) phosphonium group, a (—P(OR')$_2$) phosphonous group, a (—PR'$_2$) phosphine group, a (—NO$_2$) nitro group, a (—NO) nitroso group, a (—COOH) carboxy group, a (—COOR') ester group, a (—CHO) formyl group, a (—COR') ketone group, a —NC(O)R' group, an amino group, an ammonium group, or a (—OMe) alkoxy group, wherein R' is $C_1$-$C_5$ alkyl, $C_1$-$C_5$ perfluoroalkyl, $C_5$-$C_{24}$ aryl, $C_7$-$C_{24}$ aralkyl, or $C_5$-$C_{24}$ perfluoroaryl;

$R^5$ and $R^6$ are each $C_1$-$C_{25}$ alkyl, $C_3$-$C_{12}$ cycloalkyl, $C_5$-$C_{20}$ aryl, $C_7$-$C_{24}$ aralkyl, which are optionally substituted by at least one $C_1$-$C_{12}$ alkyl, $C_1$-$C_{12}$, perfluoroalkyl, $C_1$-$C_{12}$ alkoxy, $C_5$-$C_{24}$ aryloxy, or $C_5$-$C_{20}$ heteroaryloxy, or a halogen atom; and wherein $R^5$ and $R^6$ may be interconnected to form a cyclic system; and $R^7$ and $R^8$ are each a hydrogen atom or a $C_1$-$C_{25}$ alkyl, or a $C_3$-$C_{12}$ cycloalkyl, and wherein $R^7$ and $R^8$ may be interconnected to form a cyclic system.

3. The method according to claim 1, wherein in formula 2

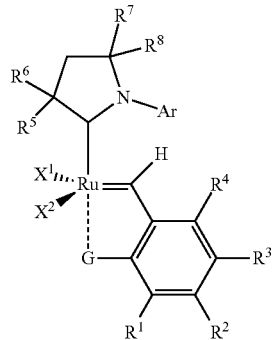

$X^1$ and $X^2$ are halogen atoms, atoms;

G is a halogen atom or a substituent selected from the group consisting of OR' and N(R')(R''), wherein R' and R'' are the same or different $C_1$-$C_{12}$ alkyl, $C_3$-$C_{12}$ cykloalkyl, or $C_5$-$C_{20}$ aryl, which are optionally substituted by at least one $C_1$-$C_{12}$ alkyl, $C_1$-$C_{12}$ perfluoroalkyl, $C_1$-$C_{12}$ alkoxy, $C_5$-$C_{24}$ aryloxy, or $C_5$-$C_{20}$ heteroaryloxy;

$R^1$, $R^2$, $R^3$, $R^4$ are each a hydrogen atom, a (—S(O)R') sulphoxide group, a (—SO$_2$NR'$_2$) sulphonamide group, a (—NO$_2$) nitro group, a (—COOR') ester group, a (—COR') ketone group, a —NC(O)R' group, an amino group, an ammonium group, or a (—OMe) alkoxy group, wherein R' is $C_1$-$C_5$ alkyl, $C_1$-$C_5$ perfluoroalkyl, $C_5$-$C_{24}$ aryl, $C_7$-$C_{24}$ aralkyl, or $C_5$-$C_{24}$ perfluoroaryl;

$R^5$ and $R^6$ are each $C_1$-$C_{25}$ alkyl, $C_3$-$C_{12}$ cycloalkyl, $C_5$-$C_{20}$ aryl, $C_7$-$C_{24}$ aralkyl, which are optionally substituted by at least one $C_1$-$C_{12}$ alkyl, $C_1$-$C_{12}$, perfluoroalkyl, $C_1$-$C_{12}$ alkoxy, $C_5$-$C_{24}$ aryloxy, or $C_5$-$C_{20}$ heteroaryloxy, or a halogen atom; and wherein $R^5$ and $R^6$ may be interconnected to form a cyclic system; and $R^7$ and $R^8$ are each a hydrogen atom or a $C_1$-$C_{25}$ alkyl, or a $C_3$-$C_{12}$ cycloalkyl, and wherein $R^7$ and $R^8$ may be interconnected to form a cyclic system.

4. The method according to claim 1, wherein in formula 2

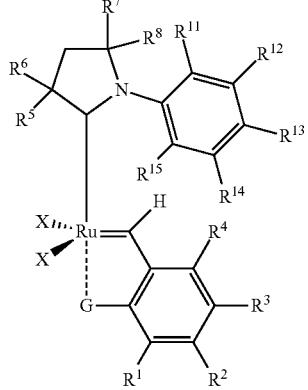

X is an atom of chlorine or iodine;

G is a halogen atom or a substituent selected from the group consisting of OR' and N(R')(R"), wherein R' and R" are the same or different $C_1$-$C_{12}$ alkyl, $C_3$-$C_{12}$ cykloalkyl, or $C_5$-$C_{20}$ aryl, which are optionally substituted by at least one $C_1$-$C_{12}$ alkyl, $C_1$-$C_{12}$ perfluoroalkyl, $C_1$-$C_{12}$ alkoxy, $C_5$-$C_{24}$ aryloxy, or $C_5$-$C_{20}$ heteroaryloxy;

$R^1$, $R^2$, $R^3$, $R^4$ are each a hydrogen atom, a (—S(O)R') sulphoxide group, a (—SO$_2$NR'$_2$) sulphonamide group, a (—NO$_2$) nitro group, a (—COOR') ester group, a (—COR') ketone group, a —NC(O)R' group, an amino group, an ammonium group, or a (—OMe) alkoxy group, wherein R' is $C_1$-$C_5$ alkyl, $C_1$-$C_5$ perfluoroalkyl, $C_5$-$C_{24}$ aryl, $C_7$-$C_{24}$ aralkyl, or $C_5$-$C_{24}$ perfluoroaryl;

$R^5$ and $R^6$ are each $C_1$-$C_{25}$ alkyl, $C_3$-$C_{12}$ cycloalkyl, $C_5$-$C_{20}$ aryl, $C_7$-$C_{24}$ aralkyl, which are optionally substituted by at least one $C_1$-$C_{12}$ alkyl, $C_1$-$C_{12}$, perfluoroalkyl, $C_1$-$C_{12}$ alkoxy, $C_5$-$C_{24}$ aryloxy, or $C_5$-$C_{20}$ heteroaryloxy, or a halogen atom; and wherein $R^5$ and $R^6$ may be interconnected to form a cyclic system;

$R^7$ and $R^8$ are each a hydrogen atom or a $C_1$-$C_{25}$ alkyl, or a $C_3$-$C_{12}$ cycloalkyl, and wherein $R^7$ and $R^8$ may be interconnected to form a cyclic system;

$R^{11}$, $R^{12}$, $R^{13}$, $R^{14}$ and $R^{15}$ are each a hydrogen atom, a halogen atom, a $C_1$-$C_{25}$ alkyl group, a $C_3$-$C_7$, cykloalkyl group, a $C_1$-$C_{25}$ alkoxy group, a $C_5$-$C_{24}$ perfluoroaryl group, $C_5$-$C_{20}$ heteroaryl group or a $C_2$-$C_{25}$ alkenyl group, and wherein the substituents $R^2$, $R^{2'}$, $R^3$, $R^{3'}$ and $R^4$ may be interconnected to form a substituted or non-substituted cyclic $C_4$-$C_{10}$ or polycyclic $C_4$-$C_{12}$ system.

5. The method according to claim 1, wherein in formula 2

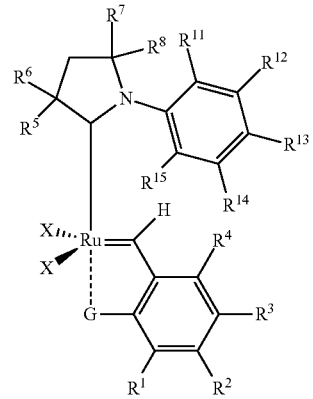

X is an atom of chlorine or iodine;

G is a halogen atom or a substituent selected from the group consisting of OR' and N(R')(R"), wherein R' and R" are the same or different $C_1$-$C_{12}$ alkyl, $C_3$-$C_{12}$ cykloalkyl, or $C_5$-$C_{20}$ aryl, which are optionally substituted by at least one $C_1$-$C_{12}$ alkyl, $C_1$-$C_{12}$ perfluoroalkyl, $C_1$-$C_{12}$ alkoxy, $C_5$-$C_{24}$ aryloxy, or $C_5$-$C_{20}$ heteroaryloxy;

$R^1$, $R^2$, $R^3$, $R^4$ are each a hydrogen atom, a (—S(O)R') sulphoxide group, a (—SO$_2$NR'$_2$) sulphonamide group, a (—NO$_2$) nitro group, a (—COOR') ester group, a (—COR') ketone group, a —NC(O)R' group, an amino group, an ammonium group, or a (—OMe) alkoxy group, wherein R' is $C_1$-$C_5$ alkyl, $C_1$-$C_5$ perfluoroalkyl, $C_5$-$C_{24}$ aryl, $C_7$-$C_{24}$ aralkyl, or $C_5$-$C_{24}$ perfluoroaryl;

$R^5$ and $R^6$ are each $C_1$-$C_{25}$ alkyl, $C_3$-$C_{12}$ cycloalkyl, $C_5$-$C_{20}$ aryl, $C_7$-$C_{24}$ aralkyl, which are optionally substituted by at least one $C_1$-$C_{12}$ alkyl, $C_1$-$C_{12}$, perfluoroalkyl, $C_1$-$C_{12}$ alkoxy, $C_5$-$C_{24}$ aryloxy, or $C_5$-$C_{20}$ heteroaryloxy, or a halogen atom; and wherein $R^5$ and $R^6$ may be interconnected to form a cyclic system;

$R^7$ and $R^8$ are each a hydrogen atom or a $C_1$-$C_{25}$ alkyl, or a $C_3$-$C_{12}$ cycloalkyl, and wherein $R^7$ and $R^8$ may be interconnected to form a cyclic system;

$R^{11}$ and $R^{15}$ are each methyl, ethyl or isopropyl; and $R^{12}$, $R^{13}$, $R^{14}$ are each a hydrogen atom, or a $C_1$-$C_{25}$ alkyl group.

6. The method according to claim 1, wherein in formula 2

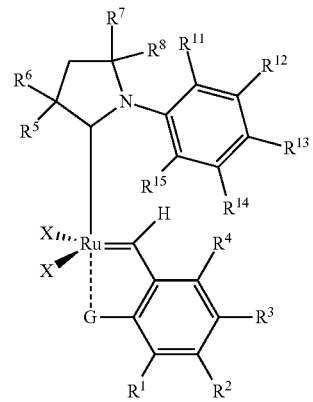

X is an atom of chlorine or iodine;

G is a halogen atom or a substituent selected from the group consisting of OR' and N(R')(R"), wherein R' is $C_1$-$C_{12}$ alkyl, $C_3$-$C_{12}$ cykloalkyl, or $C_5$-$C_{20}$ aryl, which are optionally substituted by at least one $C_1$-$C_{12}$ alkyl, $C_1$-$C_{12}$ perfluoroalkyl, $C_1$-$C_{12}$ alkoxy, $C_5$-$C_{24}$ aryloxy, or $C_5$-$C_{20}$ heteroaryloxy;

$R^1$, $R^2$, $R^3$, $R^4$ are each a hydrogen atom, a (—S(O)R') sulphoxide group, a (—SO$_2$NR'$_2$) sulphonamide group, a (—NO$_2$) nitro group, a (—COOR') ester group, a (—COR') ketone group, a —NC(O)R' group, an ammonium group, or a (—OMe) alkoxy group, wherein R' is $C_1$-$C_5$ alkyl, $C_1$-$C_5$ perfluoroalkyl, $C_5$-$C_{24}$ aryl, $C_7$-$C_{24}$ aralkyl, or $C_5$-$C_{24}$ perfluoroaryl;

$R^5$ and $R^6$ are each $C_1$-$C_{25}$ alkyl, $C_5$-$C_{20}$ aryl, which are optionally substituted by at least one $C_1$-$C_{12}$ alkyl, $C_1$-$C_{12}$, perfluoroalkyl, $C_1$-$C_{12}$ alkoxy, $C_5$-$C_{24}$ aryloxy, or $C_5$-$C_{20}$ heteroaryloxy, or a halogen atom; and wherein $R^5$ and $R^6$ may be interconnected to form a cyclic system;

$R^7$ and $R^8$ are each a hydrogen atom or a $C_1$-$C_{25}$ alkyl, and wherein $R^7$ and $R^8$ may be interconnected to form a cyclic system;

$R^{11}$ and $R^{15}$ are each methyl or ethyl; and $R^{12}$, $R^{13}$, $R^{14}$ are each a hydrogen atom, or a $C_1$-$C_{25}$ alkyl group.

7. The method according to claim 1, wherein at least one type of acyclic olefin is acrylonitrile.

8. The method according to claim 7, wherein the acrylonitrile is used in an amount of from 1 to 6 equivalents of a second acyclic olefin.

9. The method according to claim 7, wherein the acrylonitrile is used in an amount of from 1.05 to 2 equivalents of a second acyclic olefin.

10. The method according to claim 1, wherein the reaction is conducted in at least one organic solvent selected from the group consisting of toluene, benzene, mesitylene, dichloromethane, ethyl acetate, methyl acetate, tertbutyl methyl ether, and cyclopentylmethyl ether, or the reaction is conducted with no solvent.

11. The method according to claim 1, wherein the reaction is conducted at a temperature of from 20 to 150° C.

12. The method according to claim 1, wherein the reaction is conducted at a temperature of from 40 to 120° C.

13. The method according to claim 1, wherein the reaction is conducted at a temperature of from 40 to 90° C.

14. The method according to claim 1, wherein the reaction is conducted over from 5 minutes to 24 hours.

15. The method according to claim 1, wherein the compound of formula 2 is added to the reaction mixture in portions and/or continuously using a pump.

16. The method according to claim 1, wherein the compound of formula 2 is added to the reaction mixture as a solid and/or as a solution in an organic solvent.

17. The method according to claim 7, wherein acrylonitrile is added to the reaction mixture in portions and/or continuously using a pump.

18. The method according to claim 1, wherein a gaseous by-product of the reaction selected from the group consisting of ethylene, propylene, and butylene is actively removed from the reaction mixture using an inert gas or vacuum.

19. The method of claim 1, wherein the olefin metathesis reaction is a cross metathesis (CM) reaction, ring closing metathesis (RCM) reaction, or a homometathesis reaction.

* * * * *